US012622629B1

(12) United States Patent
Kocher et al.

(10) Patent No.: US 12,622,629 B1
(45) Date of Patent: *May 12, 2026

(54) DISCOVERY OF KNOWLEDGE, INTEREST AND EXPERIENCE BY PSYCHOPHYSIOLOGICAL RESPONSE

(71) Applicant: P4 X Group, Inc., Miami, FL (US)

(72) Inventors: Robert William Kocher, McLean, VA (US); Loran Dean Ambs, Williamsburg, VA (US); Marita Mariela Rance, Arlington, VA (US); Andrew Zachary Wisti, Arlington, VA (US)

(73) Assignee: P4 X Group, Inc., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/945,480

(22) Filed: Sep. 15, 2022

Related U.S. Application Data

(60) Provisional application No. 63/245,037, filed on Sep. 16, 2021.

(51) Int. Cl.
*A61B 5/377* (2021.01)
*A61B 5/374* (2021.01)
(52) U.S. Cl.
CPC .............. *A61B 5/377* (2021.01); *A61B 5/374* (2021.01)

(58) Field of Classification Search
None
See application file for complete search history.

(56) References Cited

U.S. PATENT DOCUMENTS

2019/0216356 A1 * 7/2019 Kocher .................. A61B 5/316

* cited by examiner

*Primary Examiner* — Jay B Shah
(74) *Attorney, Agent, or Firm* — Donald J. Lecher

(57) ABSTRACT

Methods are disclosed for discovery of knowledge, interest and experience of individuals indicated by measured psychophysiological response (e.g., electroencephalograph) to stimuli (e.g., images). Stimuli are selected to explore targeted topics described in various levels of detail and sub-categories organized as hierarchal trees. The degree of psychophysiological response to stimuli associated with sub-categories of topics in the hierarchal tree guides selection of additional stimuli to systematically explore hierarchal tree nodes, levels and branches to discover the extent of knowledge, interest or experience related to the targeted topic. A system enabling these methods provides archival and search of hierarchal trees associated with topics of interest, target and non-target stimuli; stimulus dataset generation, editing and presentation/application; psychophysiological data collection and processing via local and remote resources; evoked response detection, characterization and scoring; and association of indications of knowledge, interest or experience with regards to facets of the targeted topic.

4 Claims, 13 Drawing Sheets

200

205 — Expose a subject to a first sequence of stimuli

210 — Detect a brain activation response

215 — Correlate the detected brain activation response

220 — Select a second sequence of stimuli

300

305 — Expose a subject to a first stimulus of a first sequence of stimuli

310 — Detect a brain activation response

315 — Correlate the detected brain activation response

320 — Select a second stimulus of the first sequence of stimuli

325 — Expose the subject to the second stimulus of the first sequence of stimuli

FIG. 5B

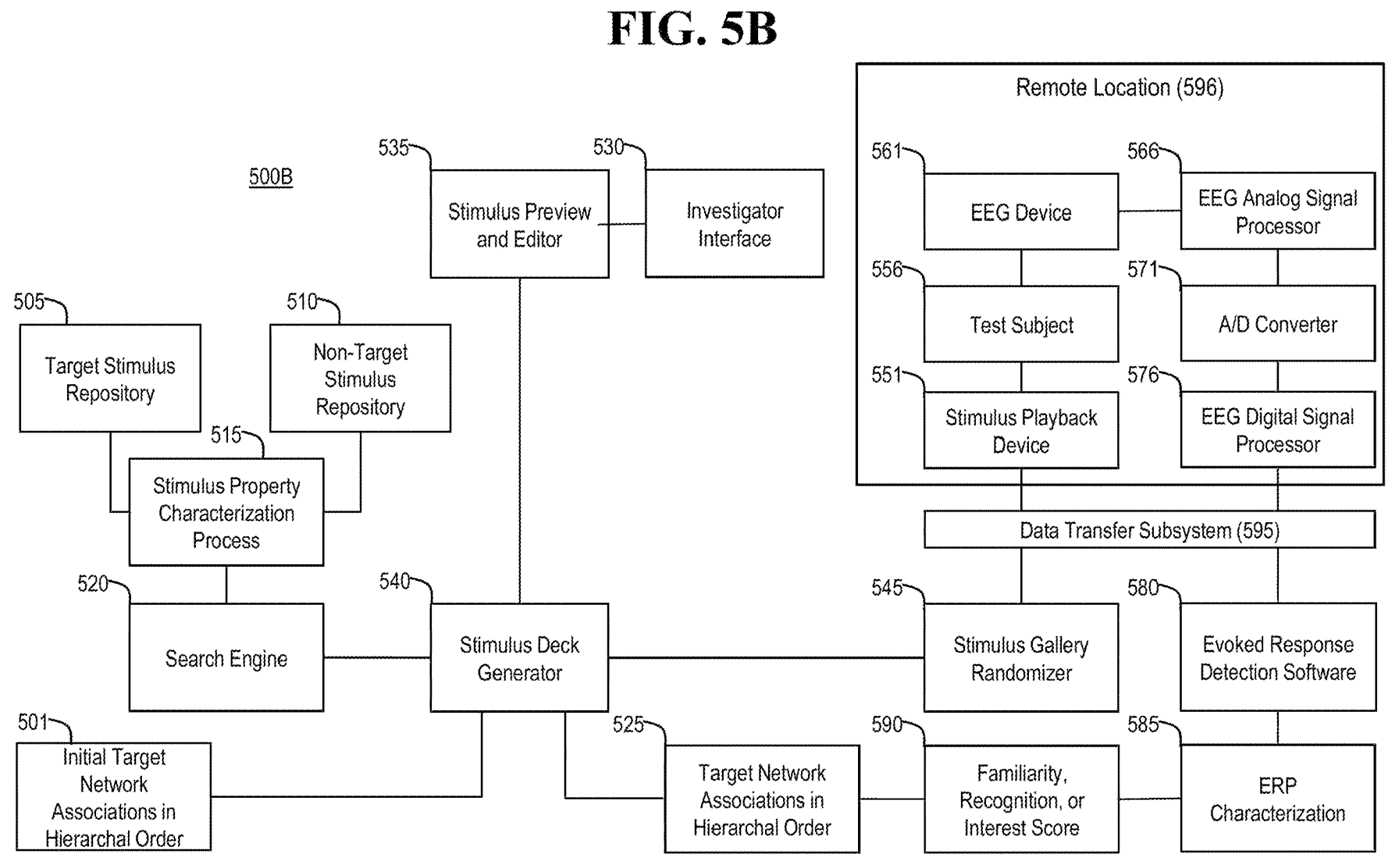

Remote Location (596)

EEG Analog Signal Processor — 566

A/D Converter — 571

EEG Digital Signal Processor — 576

EEG Device — 561

Test Subject — 556

Stimulus Playback Device — 551

Data Transfer Subsystem (595)

Evoked Response Detection Software — 580

ERP Characterization — 585

Stimulus Gallery Randomizer — 545

Familiarity, Recognition, or Interest Score — 590

Target Network Associations in Hierarchal Order — 525

Investigator Interface — 530

Stimulus Preview and Editor — 535

Stimulus Deck Generator — 540

Non-Target Stimulus Repository — 510

Stimulus Property Characterization Process — 515

Search Engine — 520

Target Stimulus Repository — 505

Initial Target Network Associations in Hierarchal Order — 501

Figure 7:
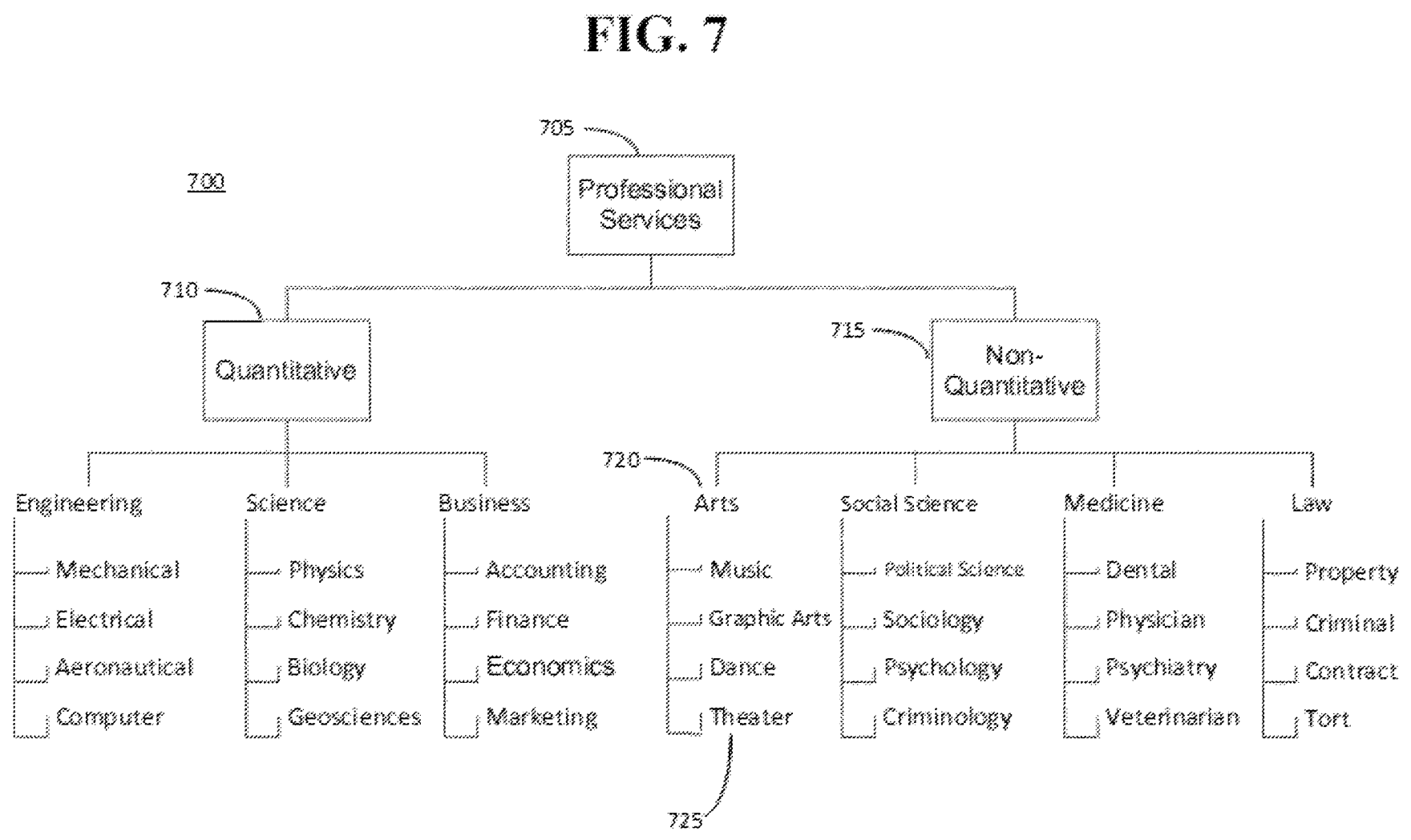

705 — Professional Services

710 — Quantitative

715 — Non-Quantitative

Engineering
- Mechanical
- Electrical
- Aeronautical
- Computer

Science
- Physics
- Chemistry
- Biology
- Geosciences

Business
- Accounting
- Finance
- Economics
- Marketing

720 — Arts
- Music
- Graphic Arts
- Dance
- Theater — 725

Social Science
- Political Science
- Sociology
- Psychology
- Criminology

Medicine
- Dental
- Physician
- Psychiatry
- Veterinarian

Law
- Property
- Criminal
- Contract
- Tort

800

<u>800</u>

DISCOVERY OF KNOWLEDGE, INTEREST AND EXPERIENCE BY PSYCHOPHYSIOLOGICAL RESPONSE

CROSS-REFERENCE TO RELATED APPLICATIONS

This application claims priority to U.S. Provisional Patent Application No. 63/245,037, filed on Sep. 16, 2021, the disclosures of each are incorporated by reference in their entirety.

FIELD OF THE INVENTION

The present invention relates to psychophysiological measurement and, more specifically, to techniques for detecting knowledge, interest or experience of a subject based on brain activation to external stimulation.

BACKGROUND

For decades Electroencephalography (EEG) and related tools that measure psychophysiological responses (e.g., polygraphs) have been used to discern whether someone is familiar with certain information. Examples of EEG tools include the systems and methods disclosed in U.S. Pat. No. 8,684,926 B2 and U.S. Patent Application publication 20140163409 A1 (each of which is incorporated by reference in its entirety). Systems such as these, are generally used in conjunction with the Guilty Knowledge Test (GKT). The purpose of the GKT is to associate the test subject to a particular event (e.g., a crime) by observation and interpretation of the test subject's psychophysiological response when confronted with information that may only be known by someone familiar with the event.

Success of the GKT requires that the investigator know about the people, places or things associated with an event in order to pose verbal or non-verbal questions to the test subject. The investigator compares the test subject's psychophysiological response to questions known to be related to the event with questions known to be unrelated to the event. The reliability of GKT test results depends upon the test administrator's knowledge of what the test subject knows or is believed to know and subjective interpretation of observed psychophysiological response of the test subject. There is a need for a non-verbal means of discovering what a person knows, is familiar with or experienced by objective interpretation of psychophysiological responses that do not rely upon a priori knowledge of what the test subject knows.

SUMMARY OF THE INVENTION

In a first example, a method is disclosed for exposing a subject to a first sequence of stimuli. At least one stimulus of the first sequence of stimuli correlated with a category of potential knowledge, familiarity or interest. Measurable brain activity of the subject to the first sequence of stimuli is detected. The detected brain activation is correlated to at least one target category, and a second sequence of stimuli is selected, based upon the observed brain activation of the subject to the first sequence of stimuli.

A system enabling the disclosed method includes one or more sensors, one or more presentation devices, and a processor. The processor is in communication with the presentation device and the at least one sensor and adapted and configured to send at least one stimulus in a first sequence of stimuli to a presentation or application device, detect brain activation from at least one sensor based upon the brain activation of a subject, correlate the detected brain activation to at least one target category, and select a second sequence of stimuli, based upon the brain activation of the subject to the at least one stimulus of the first sequence of stimuli.

For the purposes of this disclosure, a sequence of stimuli may be made up of a single stimulus or a set of stimuli.

BRIEF DESCRIPTION OF THE DRAWINGS

FIG. 5B illustrates an alternative system diagram of FIG. 5A of an example of this disclosure related to automated generation of stimulus sequences having a number of devices at one or more remote locations.

FIG. 7 illustrates a system diagram of an example of this disclosure for discovery of vocational knowledge, familiarity or interest.

DETAILED DESCRIPTION

Figure 1:
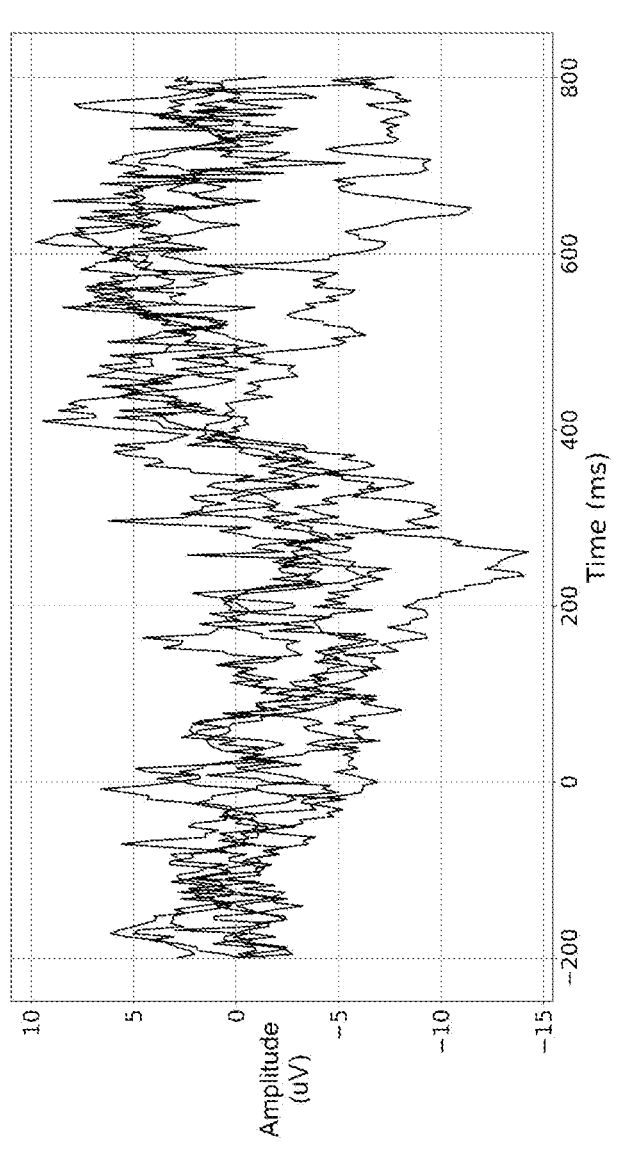
FIG. 1 illustrates the time series data from five EEG sensors illustrating the character and latency of P-300 signals indicative of knowledge, familiarity or interest.

In contrast to the GKT described above, alternative techniques, such as those disclosed herein, do not require a priori knowledge of knowledge, familiarity, or interests of the test subject. The knowledge, familiarity or interest of the test subject may be deduced without verbal questions by observing the psychophysiological response of the subject to one or more sequences of sensory stimuli (i.e. "decks") of information which may be selected based on the subject's responses to stimuli presented previously.

These stimuli can be categorized as either external or internal and may be a sensory stimulation or a neurocognitive task. External stimuli are those which are presented to a subject by an outside source. Internal stimuli are those which originate from within the brain, mind, or body. Sensory stimuli are stimuli that directly activate sensory receptors such as images, sounds, scents, tastes, vibrations, changes in temperature, pain, electrical stimulation, and/or chemical stimulation. Task stimuli aim to elicit neurocognitive processes that represent cognitive function, psychophysical processes, and neurophysiological processes.

A response of interest can either be determined from data elicited by internal, external, or task stimulation of an individual subject or a group, or it can be determined adaptively by machine learning or artificial intelligence techniques. Stimuli can be presented to the subject such as visual stimuli, or applied, such as chemical or electrical stimuli.

Sensory stimuli types include images, sounds, scents, tastes, vibrations, changes in temperature, pain, electrical/electromagnetic stimulation, photonic/laser and/or chemical stimulation. Non-sensory stimuli include neurocognitive tasks, taskless intervals of brain monitoring or intervals of monitoring the brain in response to internally generated stimuli. Task stimuli elicit neurocognitive processes that represent cognitive function, psychophysical processes, and neurophysiological processes.

Other stimulation methods might be employed to stimulate various sensory neurons evoking corresponding sensations. Sensations may include mechanical (e.g. vibration, pressure), nociceptive, temperature, itch, auditory, gustatory, proprioceptive, stimulation of the vestibular sense, kinesthetic stimulation, olfactory components or any combination thereof. A specific sensation might be evoked by different methods, e.g. the sensation of "itch" might be caused by electrical stimulation or the application of chemicals, the sensation of "hot" might be caused by the application of a hot element to the body or electrical or chemical stimulation and so forth.

Psychophysiological signals of interest may include, but are not limited to, signals associated with neurophysiological responses such as localized or global changes in measures of brain activity, directly or indirectly quantifiable, such as blood flow and related changes, blood oxygenation/hemoglobin concentration, changes in magnetic field or changes in light-absorption spectra, metabolic rates, or changes in the emission of energy by radioactive substances, changes in electromagnetic properties of single neurons or multitude of neurons, changes in ratios of chemical components or the production/release of chemical components by single cells or a multitude of cells, localized or global measures of morphology and physiology and changes thereof, measured by changes in brain structure including myelination, cortical thickness, structural connectivity, the central nervous system, and the peripheral nervous system; signals associated with psychophysiological responses such as pupillometry, eye movement activity, direction-of-gaze activity, electrodermal activity, muscle activity, cardiography, heart rate activity, heart rate activity variability, blood pressure monitoring and respiration rate activity; signals associated with psychological responses such as indicators of personality, learning styles, memory, executive function, response inhibition; signals associated with psychophysical responses such as reaction time, signal detection; physiological changes such as hormone levels, blood glucose levels, oxygenation; and other markers distinguishing individuals and/or groups such as vocational skills.

Research has established that a test subject's degree of familiarity with external stimuli such as images and sounds is correlated to a number of responses of interest, among those strength and timing of brain activation observed by electroencephalograms (EEGs). The human brain may absorb and process stimuli at very high rates of presentation. Visual stimuli may be presented rapidly in a technique known as Rapid Serial Visual Presentation. In addition to images, external stimuli such as auditory, mechanical, chemical, vibrational, nociceptive, proprioceptive, thermal, olfactory, and gustatory stimuli may be presented using an analogous rapid serial presentation technique (collectively, the rapid serial presentation of any stimuli are referred to herein as "RSP"). The RSP technique typically displays stimuli to a test subject at rates of 4 to 12 stimuli per second. Depending upon the content and complexity of the information presented and the ability of the test subject to process the information, the presentation rate may be more or less than the typical values.

The brain processes stimuli and produces psychophysiological responses to recognition of, familiarity with or interest in the stimuli in the form of brain activation waves observed by EEG. By way of example, a response pattern strongly associated with recognition and familiarity is the "P-300" psychophysiological signal which has a characteristic positive deflection observed within a range of 250 to 600 milliseconds (ms) after being exposed to a recognized stimulus. Another indicator of interest is attention, as seen in a global reduction of power in the alpha frequency band of the EEG signal. EEG or other psychophysiological data time-tagged with the display of sensory stimuli presented by the RSP technique enables a subject to be exposed to a large number of sensory stimuli on a particular topic in a relatively short period of time. For instance, assuming a presentation pattern of 3 seconds of display followed by 3 seconds of rest, and a display rate of 8 images per second, a subject may be exposed to 240 images per minute. Another example of a feature of brain activity associated with attention which is an indicator of interest would be alpha synchrony and power in certain brain areas, characterized by synchronous activity in EEG in a specific frequency range.

EEG may be quantified in various ways in the time domain, and also in the time-frequency domain, for example, by applying a Fourier transformation, including by amplitude, power, frequency, and in order to generate numerical values, ratios, or percentages; graphically display arrays or trends; and set thresholds. Many quantitative EEG measures may be used to quantify slowing or attenuation of faster frequencies in the EEG. These include the calculation of power within different frequency bands (i.e., delta, theta, alpha, and beta); ratios or percentages of power in specific frequency bands; and spectral edge frequencies (based on the frequency under which x % of the EEG resides). These discrete values may then be compared between different regions, such as hemispheres, or between electrode-pair channels.

Additionally, analyzing current source density, the location or origin of aspects of the EEG signal may be estimated. Incorporating this information, filtered by the contribution of each channel to a measure of interest, the connectivity and composition of networks may be estimated and compared between different stimuli and subjects. Such networks may also be identified using EEG signals acquired from the subject at rest before or after stimulus presentation and may explain variance within subjects and between subjects.

Time-compressed spectral arrays ("Spectrograms") incorporate both power and frequency spectrum data and may be represented using color to show power at different frequencies as a function of time. Additional measures include amplitude integrated EEG, which continuously monitors brain activity by average ranges of peak-to-peak amplitudes displayed using a logarithmic scale, and the commercial Bispectral Index. Other nonparametric methods exist beyond Fourier transformation, including interval or period analysis and alternative transformation techniques. Parametric, mimetic, and spatiotemporal analyses are also available using a variety of computational methods and waveform analysis based on machine learning approaches trained on EEG recordings and other responses of interest. Basic measures of total power may be quantified and compared to performance characteristics to identify correlations that may be used to predict the reoccurrence of those performance characteristics.

Recognition, familiarity, or interest may also be indicated by changes in other aspects of the EEG signal in the time domain, the time-frequency domain, (such as changes in the power of one or more frequency bands, or the changes in the overall power distribution across frequencies), spatial distributions of such features, as well as changes in second level analysis results such as changes in functional or effective connectivity between two or more regions or differences in detected networks. In addition to artificial intelligence, machine learning and deep learning techniques for extracting indications of recognition, familiarity and interest or other forms of processing from time series data, various approaches of network analysis, spatiotemporal signal processing, and temporal complex network analysis may be employed. Signal processing may discriminate between brain activation indicating recognition, familiarity and interest or other forms of processing such as familiarity with the stimulus presented, (e.g., images or sounds), and non-recognition, unfamiliarity or non-interest with the stimuli. The character, (e.g., frequency, amplitude, latency, location and spatiotemporal distribution), of the P-300 component varies by individual, the sense stimulated, (e.g., visual, auditory), and with time for any particular individual. FIG. 1 illustrates an EEG time series of five visual target trials from a representative subject, and depicts the trial-to-trial variability of amplitudes and latencies for the P-300 component, (Wang and Ding, Clinical Neurophysiology, Volume 122, Issue 5, May 2011, Pages 916-924).

Brain activation during recognition also has repeatable and predictable characteristics which may be exploited by digital signal processing algorithms. The brain activation discriminator, often referred to as the classifier component, may be trained in the characteristic nature of the test subject's EEG response when presented with stimulus records or targets known to be familiar to the test subject. The response to such target records provides the classifier component with exemplar characteristics to discriminate records that are not known to be known by the test subject but probe what the test subject recognizes. Alternatively, the classifier component may learn the difference between recognition and non-recognition brain activation by observing the brain activation in response to a deck containing stimuli that are not necessarily known to be known by the test subject but are likely to be recognized. Examples might include images of famous persons or an image of the test subject.

Depending upon the individual test subject and the type of stimuli presented, brain activation indicative of recognition in the P-300 may vary in amplitude, character, and latency. A brain activity classifier component algorithm may correlate indications of recognition in brain activation other than the typical P-300 to strengthen the confidence in recognition or non-recognition. Additionally, features other than the P-300, e.g. features in the frequency domain or in the time-frequency domain, or features present exclusively or most strongly at one or more electrodes corresponding to coordinates on the brain, might be identified to be indicative of recognition, interest, or familiarity.

A test subject may intentionally or unintentionally create circumstances that adversely affect EEG or other psychophysiological data such that EEG recognition, interest, or familiarity signals are suppressed, masked, or otherwise corrupted. A test-subject that becomes inattentive or intentionally suppresses the senses targeted by the stimuli (e.g., for visual stimuli, averting eyes from display) may not produce responses indicating recognition. Brain activation indications of inattentiveness and external indications of suppressed senses may be used to flag the recognition scoring algorithm to disregard those tests. When the test subject is again attentive to the stimuli, the recognition scores may again be useful indicators of recognition.

Likewise, intentional or unintentional masking of some psychophysiological signals may be accomplished by muscle movements in the face and scalp. EEG signals associated with muscle movement is typically much larger than EEG signals resulting from brain functions. Signals resulting from eye blinks, jaw clinching or scalp motion may be automatically discriminated from measurable brain activity and therefore used to adjust recognition scores for target and non-target stimuli.

Presentation of a particular deck containing a set of stimuli or individual stimuli within the deck may be repeated more than once to strengthen statistical confidence in the EEG indications of recognition, familiarity or interest with a particular stimulus. Shuffling the deck, (i.e., reordering the target and non-target stimuli), each time the deck is presented ensures that the brain activation observed for target stimuli are due to the content of the stimulus rather than the presentation order of the stimuli. Repositories holding stimulus datasets may consist of datasets or single stimuli of various modalities.

Figure 2:
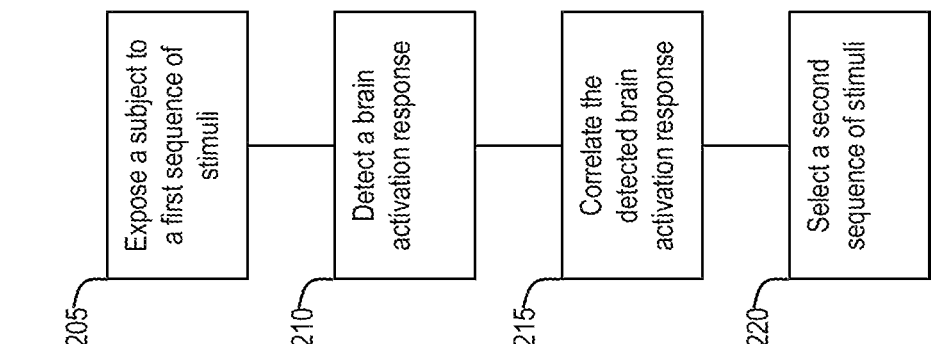
FIG. 2 illustrates a flow diagram for a first method for knowledge, familiarity or interest detection.

The general features of this disclosure provide for an automated method that characterizes brain activation from EEG or other psychophysiological data to indicate the level of recognition of sensory stimuli presented in multiple sequences of sensory stimuli that are presented to the test subject. The system may have access to category repositories of target stimuli and non-target stimuli. Target stimuli may represent information, which would be valuable to know that the subject possesses. Non-target stimuli represent information, which generally would not be thought to be valuable to know that the subject possesses. Automated indication of recognition of target stimuli in one deck may guide automated selection of target stimuli in subsequent decks to obtain additional detail of the subject's knowledge, familiarity, interest, and experience. Within the broad target and non-target categories are further categories of sensory stimuli, which may be classified according to the topics or subject matter to which they are related. Decks may be first presented to the test subject with stimuli that cover broad subject areas covering major divisions of a topic. Depending upon which stimuli records result in brain activation indications of recognition or other indicators of processing, subsequent decks with stimuli covering similar or related topics in greater detail and specificity may be selected and presented to the test subject to discover additional knowledge, familiarity, interest, and experience FIG. 2 shows a flow diagram of an example of this disclosure for a method 200 to detect knowledge, familiarity or interest of a subject by exposing the subject to stimuli and correlating certain detected brain responses to categories correlated with the stimuli presented. The subject is exposed to the first sequence of sensory stimuli 205. Each stimulus of the first sequence of sensory stimuli is correlated with a category related to a topic of knowledge, familiarity or interest. A brain response of the subject to each stimulus of the first sequence of sensory stimuli is detected 210, and, based on the occurrence a feature of the EEG signal linked to recognition, familiarity, or interest, such as the P-300 signal, the detected brain activation is correlated 215 to at least one target category. In an example the method may further comprise selecting a second sequence of sensory stimuli 220, based upon the brain activation of the subject to each stimulus of the first sequence of sensory stimuli.

Brain activity, measurable with EEG can include features in the time domain, the frequency domain, the time-frequency domain, added measures of spatial location, coherence features and the combination of these features leading to indicators of connectivity and networks. In addition, features may be "learned" by AI/ML. Time domain features include changes in voltage compared to baseline occurring at a specific time. Frequency domain features include the amplitude and phase in a specific frequency. Time frequency domain features include changes in frequency, amplitude, phase and power in time. Changes in any EEG measurable features can vary in different sensors, i.e. locations above the brain. Including location information allows for the determination of coherence measures and connectivity which are the basis of network analyses.

Figure 3:
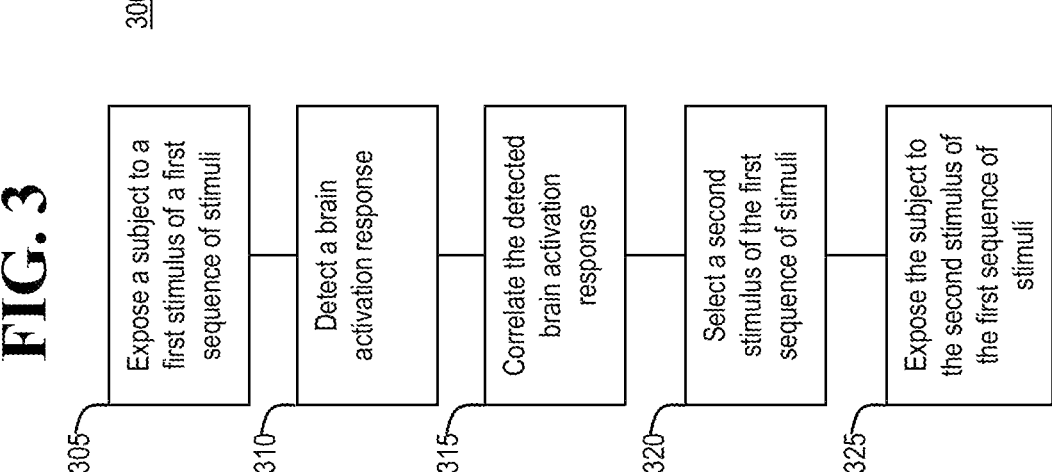
FIG. 3 illustrates a flow diagram for a second method for discovery of knowledge, familiarity or interest.

FIG. 3 shows a flow diagram of another example of this disclosure for a method 300 to detect knowledge, familiarity or interest of a subject by exposing the subject to stimuli and correlating certain detected single features of brain activation or a combination or weighted combination of features to categories correlated with the stimuli presented. At least one stimulus of the first sequence of sensory stimuli is correlated with a category. In some examples there may be many categories, such as those related to the lower levels of abstraction in the vocational knowledge and experience discovery example discussed below. The subject is exposed to a first sequence of sensory stimuli 305. Brain activation is detected 310, and, based on the occurrence of a stronger discernible P-300 signal (for example), the detected brain activation is correlated 315 to the target category. A second sequence of stimuli may be selected 320 and exposed 325 to the subject based upon brain activation in response to the first sequence of stimuli. It is also possible to enhance features of familiarity or interest by contrasting brain activation in response to stimuli of a specific category with brain activation of stimuli with similar characteristics but not being members of a single category.

Figure 4:
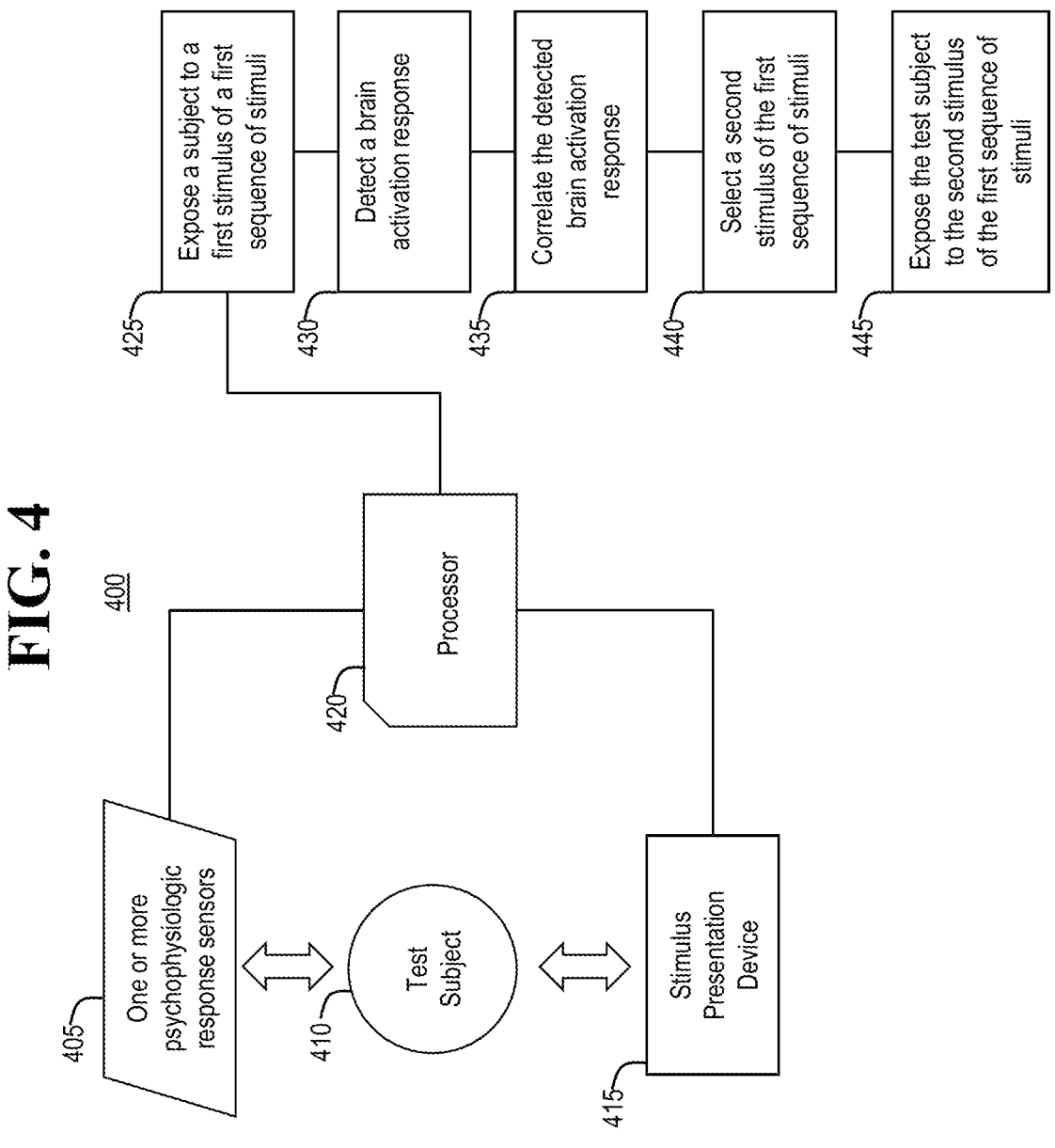
FIG. 4 illustrates a system diagram for a method for discovery of knowledge, familiarity or interest.

FIG. 4 shows a system diagram of another example of this disclosure for a method 400 to detect knowledge, familiarity or interest of a subject by exposing the subject to stimuli and correlating certain detected brain activations to categories correlated with the stimuli presented. This example includes one or more sensors 405. These sensors may be electrodes or any other component suitable for detecting psychophysiological signals. Electrodes may be individually wired or part of a connected array. The sensors may be any that are suitable to take a reading from a human subject 410. Typically, but not necessarily, the sensors may be placed on the scalp with a conductive gel or paste. Caps, netted devices or dry sensors may also be used. A presentation/application device 415 is included, such as an audio video system, computer, or similar device capable of generating stimuli that may be experienced by a subject. The presentation/application device may also be any device suitable for generating and/or applying stimuli such as chemical, electrical, auditory, gustatory, mechanical, vibration, nociceptive, thermal, visual, olfactory stimuli, or any combination thereof. A processor 420 is also included for executing instructions stored in a memory to cause the processor to perform the functions disclosed in this disclosure, for example, to expose the subject to a first stimulus of a first sequence of sensory stimuli 425 through the presentation/application device. At least one stimulus of the first sequence of sensory stimuli is correlated with a category. Non-target stimuli may be similar to target stimuli for a particular subject matter category but not necessarily representative of that category. The processor detects 430 brain activation of the subject to each stimulus of the first sequence of sensory stimuli and, based on the occurrence of a P-300 signal when analyzed together with the other stimuli that are part of the target category, the detected brain activation is correlated 435 to at least one target category.

More generally, a subject such as a person may be exposed to a first sequence of sensory stimuli. The person may be exposed to the stimuli at a rate of at least 3 stimuli per second, although significantly slower rates are also contemplated herein. The first sequence may have one or more stimuli. A stimulus may be a sight stimulus, a sound stimulus, a touch stimulus, a smell stimulus, and a taste stimulus or any combination thereof. One or more than one of the stimuli in the first sequence may be associated with a category. For example, a single stimulus such as a photograph of a football game, may be associated with a category such as a "football." The category may be an occupational category, such as "football player" or "referee." Likewise, a group of sensory stimuli may be associated with a category. For example, a photograph showing a football game, a photograph showing a bicycle race and a photograph showing a tennis match may be associated as a group with a category, such as "sports." The category may be an occupational category, such as "athlete."

Brain activation of the subject to stimuli may be detected using sensors. The response may be a P-300 signal. The response may be correlated to at least one target category. A second sequence of sensory stimuli may be selected based upon the brain activation to one or more stimuli in the first sequence. The second stimuli may be selected automatically or by a user. The first sequence of sensory stimuli may be a baseline sequence.

Proper assembly of the sequence of a deck is a key contributor of the certain examples of this disclosure. A test deck may be composed of a small number of target stimuli used to probe the test subject's familiarity or interest in a topic or range of topics, and a larger number of non-target items unlikely to be recognized by the test subject but similar in gross characteristics of the target items. For example, the ratio of target to non-target items may range between 1:25 to 1:2, but many other ranges are possible including the target stimuli being more frequent than the non-target items. When the targets are used to isolate topics of familiarity in a deck that covers a broad range of topics the ratio of targets to non-targets may be larger because many more of the intended probing target stimuli may also be unfamiliar to the test subject. The size of decks at a particular level of abstraction may be small or large. The deck may be broken into subsets or hands to accommodate the attention span of the test subject or allow more frequent periods of rest between hands. Other methods of presenting stimuli, e.g. oddball paradigms, that are often associated with novelty of stimulus, might use different ratios. In the case where no prior knowledge of the subject's knowledge, interest, or familiarity is available, an a priori ratio cannot be determined. Alternatively, stimuli might be presented in 2 specific frequencies. Other presentation scenarios are also possible.

As stated above, comparison of brain activation for target and non-target stimuli provides insight into the test subject's knowledge, familiarity or interest in a subject. In an example where the stimuli are images, target and non-target images in the deck may be selected from images of people, places, things, numbers, letters, words, and symbols. Target and non-target images in the deck are selected to be similar in physical attributes such as size, color, resolution, and composition. In an example where the stimuli are auditory, examples may include audio clips, voice, music, and the sounds that relevant things make. Similar to visual presentation decks, auditory decks are more diagnostic if target and non-target clips are similar in attributes such as volume level and background noise levels. This minimizes the occurrence psychophysiological responses that may be more strongly associated with surprise or startle than with the desired response of recognition.

Figure 5A:
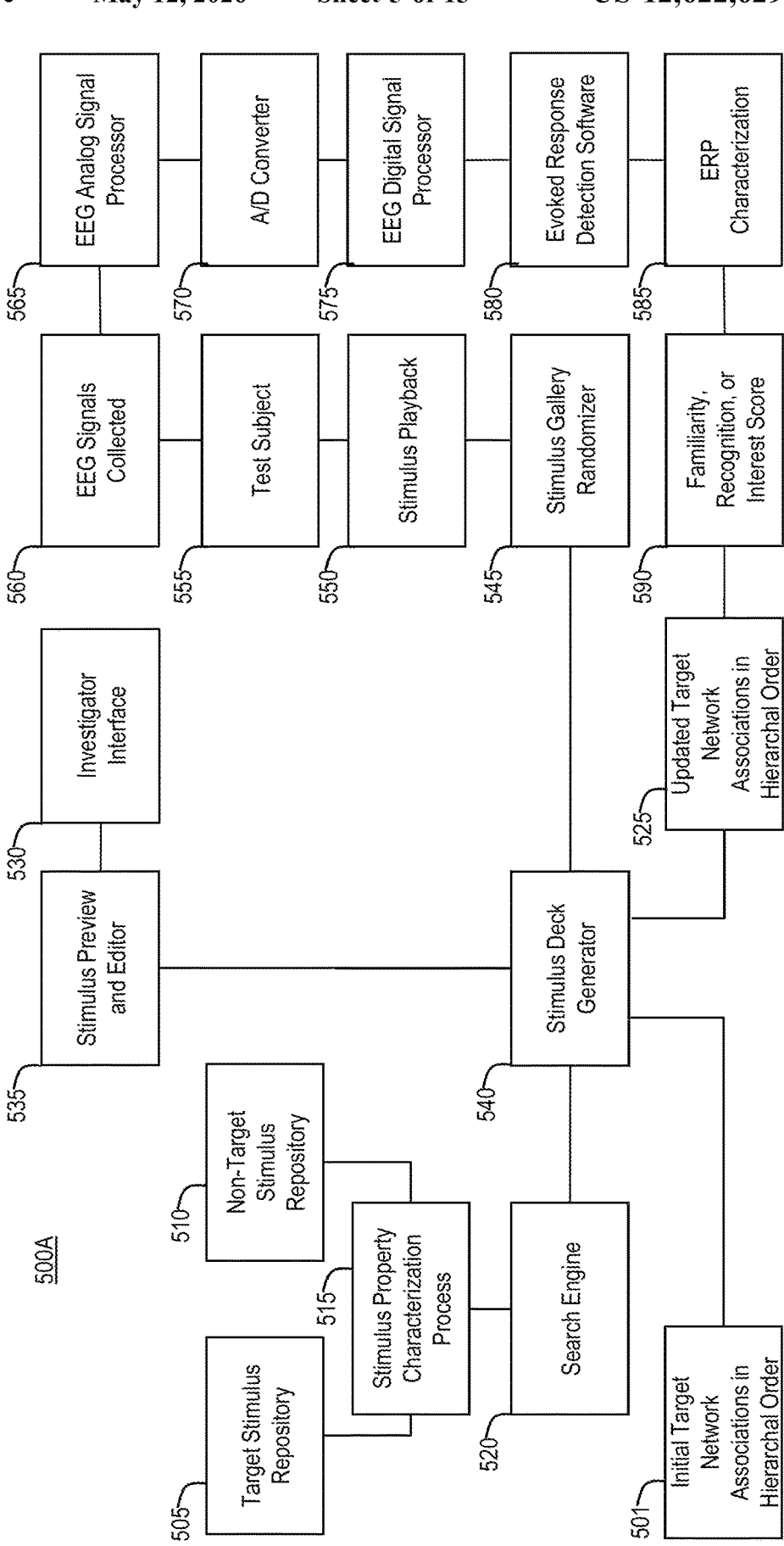
FIG. 5A illustrates a system diagram of an example of this disclosure related to automated generation of stimulus sequences.

Decks designed to explore the depth and breadth of familiarity or interest of a particular category may be compiled beforehand or created on the fly by an automated system that employs machine learning techniques to populate new decks of sensory stimuli based on indications of familiarity observed in previous decks of sensory stimuli. FIG. 5A depicts one example wherein new decks may be generated to validate what was indicated as familiar in earlier decks (e.g., via Initial Target Network Associations, 501) and introduce new stimuli that probe a deeper level of knowledge on topics of familiarity. In some scenarios of operation, the Initial Target Network Associations 501 may not provide any indications of prior target associations with topics of familiarity which will require the Stimulus Deck Generator 540 to select stimulus sequences to discover the test subject's areas of familiarity or interest at a very high level of abstraction. FIG. 5A shows a system diagram 500A, where target stimuli 505 and non-target stimuli 510 may be characterized by characterization process 515 and made accessible to search engine 520. Stimulus deck generator 540 draws a sequence of sensory stimuli from the search engine and sends the sequence to the randomizer 545. Optionally, a user may access the sequence of sensory stimuli through the investigator interface 530 and edit the sequence through the stimulus preview and editor 535. It is also possible to have the randomizer present stimuli in a structured or partially-randomized way.

The investigator interface 530 is the interface between the system operator and the system 500A. The investigator interface 530 provides a means of reporting system status, alerts and processing results to the operator and enables the operator to monitor system performance, conduct data entry and editing, and control processing flow. The stimulus preview and editor 535 enables the operator to preview the contents of stimulus datasets, edit the contents, modify the order of presentation, configure the presentation and conduct file management of the stimulus datasets.

The stimuli are then presented 550 to the test subject 555, and the subject's EEG signals are collected 560, analog processed 565, converted 570, and digitally processed 575. The P-300 signal, as an example of a feature of interest within the EEG dataset, may be detected 580, characterized 585, scored 590, and entered into a hierarchy of scores 525 for target stimuli. The stimulus deck generator may then draw on the previous target hierarchy to generate more relevant decks for further presentation/application to the subject. For example, the stimulus deck generator may select target stimuli of the same categories as those that are near the top of the target stimuli hierarchy. This process may also be performed after each stimulus is presented, such that the deck generator may continuously improve the relevancy of the target stimulus to be presented within a given deck.

FIG. 5B depicts an alternative method 500B of the method 500A of FIG. 5A, wherein a data transfer subsystem 595 may communicate with a remote location 596. The data transfer subsystem 595 may include hardware and/or communication software that allows communication through, a local area network (LAN), a wide area network (WAN), an internet area network (LAN), and/or a computer network using Transmission Control Protocol (TCP) or Internet Protocol (IP) protocols to communicate between a plurality of networks and devices.

FIG. 5B illustrates a system diagram 500B, where target stimuli 505 and non-target stimuli 510 may be characterized by characterization process 515 and made accessible to search engine 520. Stimulus deck generator 540 draws a sequence of sensory stimuli from the search engine and sends the sequence to the randomizer 545. Optionally, a user may access the sequence of sensory stimuli through the investigator interface 530 and edit the sequence through the editor 535, as described above in FIG. 5A. The stimuli are then communicated through a data transfer subsystem 595 to be presented on a stimulus presentation/application device 551 to the subject 556, and the subject's EEG signals are collected on a EEG recording device 561 that records one or more areas of the brain in time and location, Brain activation is analyzed (number). As an example, the P-300 signal may be then communicated back to the data transfer subsystem 595 and detected by the evoked response detection software 580, characterized by the evoked response potential (ERP) characterization 585, scored with a familiarity, recognition or interest score 590, and entered into target network associations of scores in hierarchal order 525 for target stimuli. As previously disclosed, the stimulus deck generator 540 may then draw on the previous target hierarchy 525 to generate updated and more relevant decks for further presentation/application to the test subject. For example, the stimulus deck generator 540 may select target stimuli of the same categories as those that are near the top of the target stimuli hierarchy 525. This process may also be performed after each stimulus is presented, such that the deck generator 540 may continuously improve the relevancy of the target stimulus to be presented within a given deck.

Brain activity can be recorded by brain activation recording device. Examples of such devices include an EEG amplifier or an MRI receiver coil. Brain activity can be recorded with regard to temporal, spatial, and intensity properties. An example might be a changing voltage signal in a sensor at a specific location in relation to the brain, or changes in blood oxygenation level at a specific location in the brain.

Figure 6A:
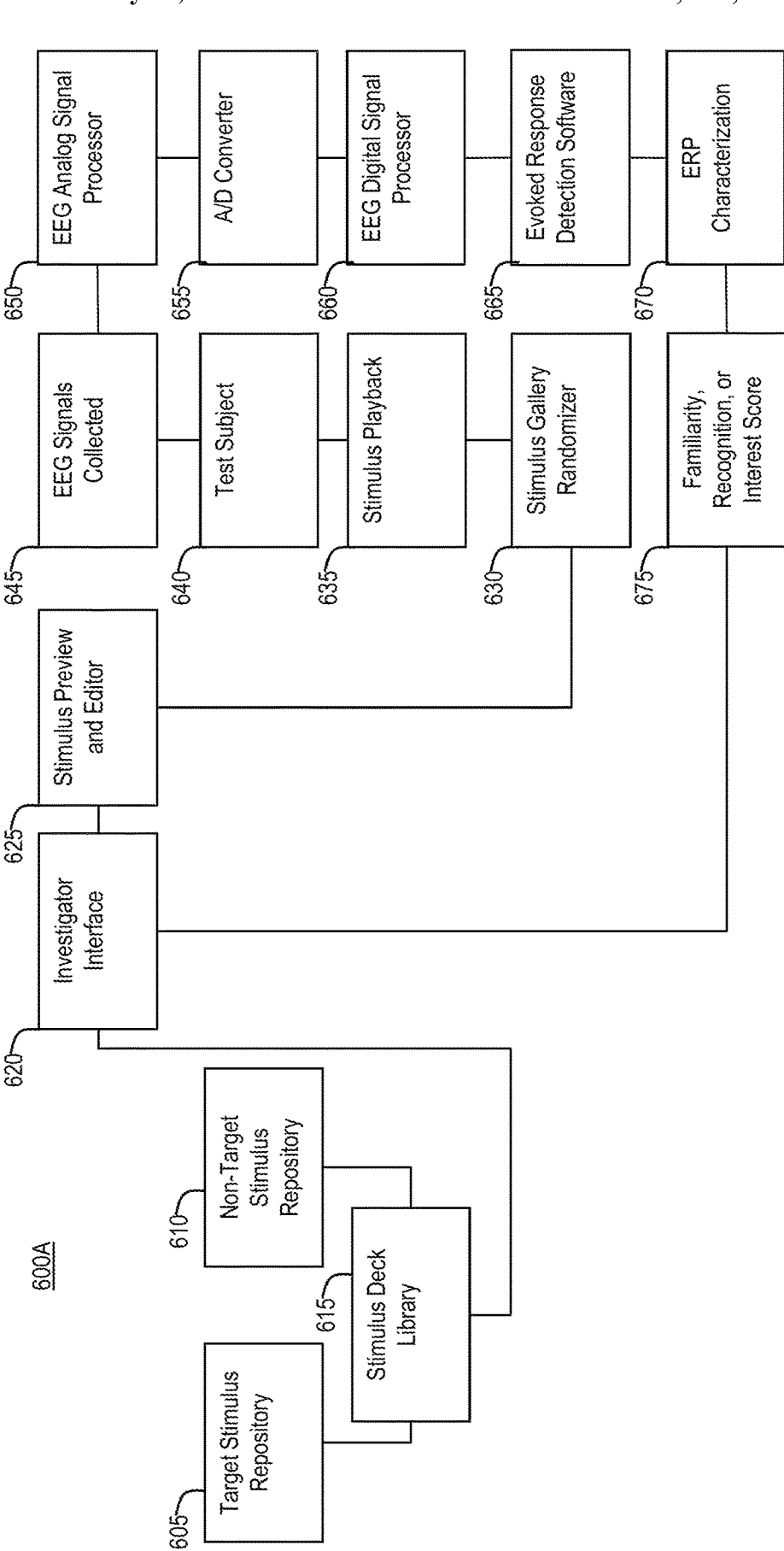
FIG. 6A illustrates a system diagram of an example of this disclosure related to discovery of vocational knowledge, familiarity or interest.

Alternatively, it may be advantageous for the deck to be manually compiled by a user (e.g., an investigator). FIG. 6A depicts one such example. In this system diagram example 600A, a user may compile a stimulus deck by accessing, through investigator interface 620, the stimulus deck library 615 that draws on target stimuli 605 and non-target stimuli 610. The investigator interface 620 is the interface between the system operator and the system 600A. The investigator interface 620 provides a means of reporting system status, alerts and processing results to the operator and enables the operator to monitor system performance, conduct data entry and editing, and control processing flow. The stimulus preview and editor 625 enables the operator to preview the contents of stimulus datasets, edit the contents, modify the order of presentation, configure the presentation and conduct file management of the stimulus datasets.

The investigator may compile and edit the deck via editor 625 and then enter the deck into randomizer 630. The stimuli are then presented 635 to the subject 640, and the subject's EEG signals are collected 645, analog processed 650, converted 655, and digitally processed 660. The P-300 signal may be detected 665, characterized 670, and scored 675. The user then has access to the scoring through the investigator interface.

Figure 6B:
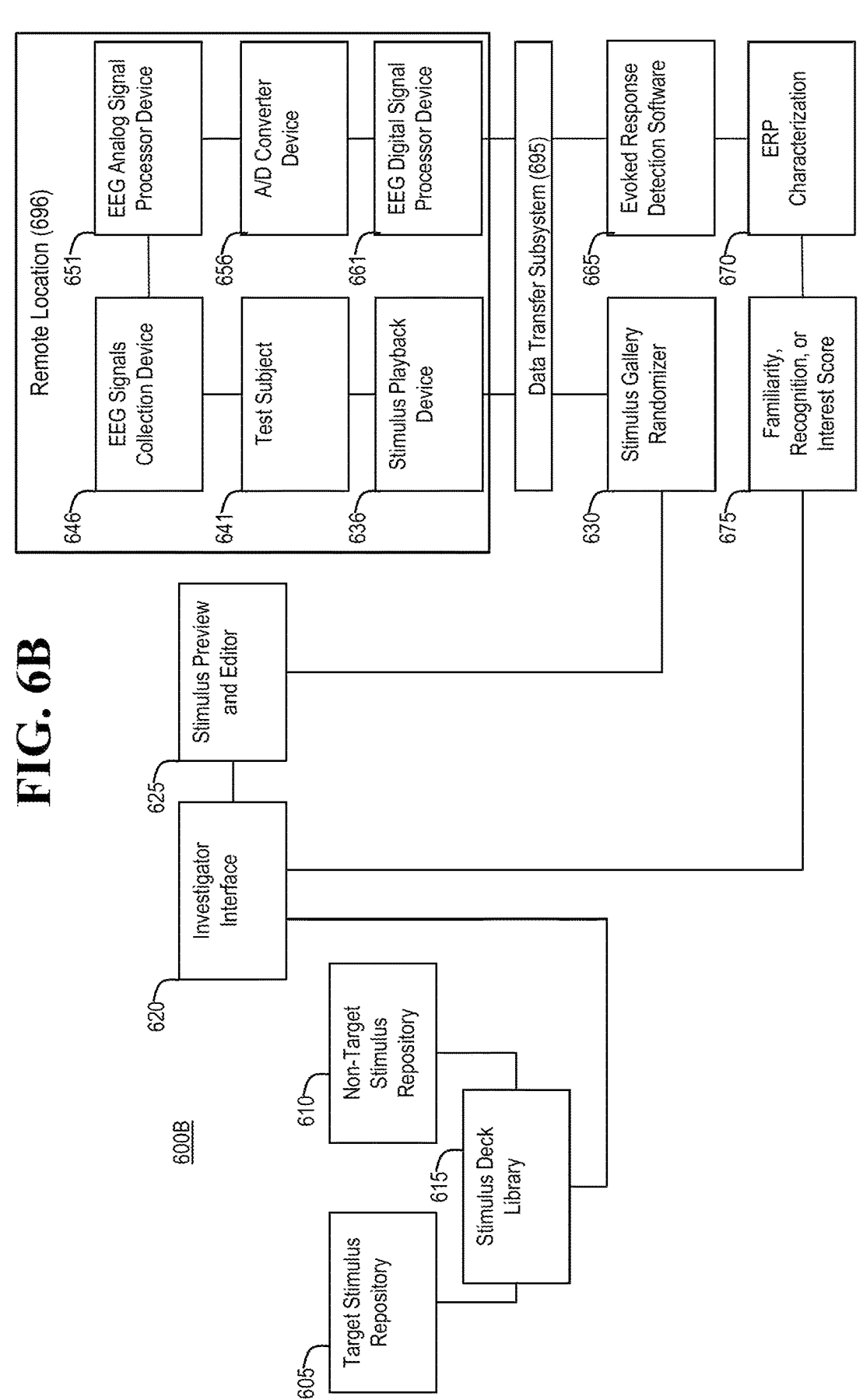
FIG. 6B illustrates an alternative system diagram of FIG. 6A of an example of this disclosure related to discovery of vocational knowledge, familiarity or interest having a number of system components at a remote location.

FIG. 6B depicts an alternative method 600B of the method 600A of FIG. 6A, wherein a data transfer subsystem 695 may communicate with a remote location 696. The data transfer subsystem 695 may include hardware and/or communication software that allows communication through, a local area network (LAN), a wide area network (WAN), an internet area network (IAN), and/or a computer network using Transmission Control Protocol (TCP) or Internet Protocol (IP) protocols to communicate between a plurality of networks and devices.

FIG. 6B illustrates a system diagram 600B, where a user may compile a stimulus deck by accessing, through investigator interface 620, the stimulus deck library 615 that draws on target stimuli 605 and non-target stimuli 610. The investigator may compile and edit the deck via editor 625 and then enter the deck into randomizer 630. The stimuli are communicated to the data transfer subsystem 695 and then presented at the remote stimulus/presentation/application device 636 to the subject 641, and the subject's EEG signals are collected by an EEG signals collection device 646, the EEG signals are analog processed by an EEG analog signal processor device 651, converted by an A/D converter device 656, and digitally processed by an EEG digital signal processor device 661. The P-300 signal as an example may then be communicated back via the data transfer subsystem 695 to be detected by the evoked response detection software 665, characterized via an ERP characterization process 670, and scored with a familiarity, recognition or interest score 675. The user then has access to the scoring through the investigator interface 620.

The methods of 600A and 600B are suitable for a variety of applications with the objective of discovering the knowledge, experience, or interest of a person. Examples include, but are not limited to, discovery of education topics, training and education retention, pre-employment evaluation, resume validation, vetting undocumented claims of knowledge, interest, and experience, vocational counseling and guidance, criminal investigation and interrogation.

As shown in FIG. 7 and discussed below, another example of this disclosure is described in relation to vocational knowledge and experience detection 700. The purpose of this example is to identify the vocational training of a test subject.

Multiple decks of sensory stimuli are presented to the test subject at various levels of abstraction or detail in order to guide selection of topics of later decks with increased level of detail, and which further narrow the scope of the search. The lower level decks 720 have increased resolution and specificity of characteristics or knowledge and experience unique to specific professions. In this example, the first level of abstraction is to determine if the test subject operates in a quantitative 710 or non-quantitative 715 division of professions—a very high level of abstraction. From there, decks are presented to the test subject to determine which category of profession (e.g. 720) within the quantitative or non-quantitative division the test subject operates. Examples of professional disciplines are engineering, medicine or the arts. Once the category is determined, decks of stimuli for specific professions (e.g. 725) such as mechanical engineer, graphical artist or criminal lawyer are present to establish the specific profession of the test subject. This simple three-tiered example (i.e., division, discipline, and specific profession) is not intended to describe the full breadth and depth of potential vocational applications.

At the highest level of abstraction, the division level, test decks are compiled to establish quantitative or non-quantitative division of professions. Other ways to differentiate divisions at this level are also possible. Example content of decks of target stimuli might include: names of principal concepts or persons key to specific professional disciplines, technical terms unique with quantitative and non-quantitative disciplines, fundamental equations used in quantitative professional disciplines, mathematical constants used in the quantitative professions, symbols commonly used in quantitative and non-quantitative disciplines, or acronyms commonly used in quantitative and non-quantitative disciplines. If the stimulus dataset dealer is a user, she may be in proximity with the test subject as the decks are presented. Alternatively, the stimulus dataset dealer may be located remotely and monitor events by electronic communications.

This approach to vocational evaluation does not rely on binary decision of familiar or not familiar with a particular person, place, or thing as in the GKT. Instead, this technique uses multiple steps with increasing level of detail to discover the profession of a test subject without knowing anything about the test subject beforehand. The progression to each lower level of detail is guided by the positive response of familiarity with one or more targets in the test deck at a higher level of abstraction to discover areas of knowledge, familiarity or interest of a subject. Based upon response to stimuli, the administrator (the stimulus dataset dealer) selects another deck to ascertain familiarity with increased detail to further refine the depth and breadth of familiarity with related topics. As discussed above, the stimulus dataset dealer may be a user or automated.

In another example, an EEG method is disclosed, comprising: sensors, amplifiers, analog filters, Analog to Digital converters, digital filters, noise rejection components, and signal extraction processing components; a stimulus presentation/application system capable of reproducing images, video, and sounds, synchronized in time with the sensors, implemented with one or more decks of analog or digital stimulus files which are reproduced serially for reception by human senses and elicit psychophysiological response recorded by the EEG system, wherein the stimulus decks are presented systematically in order of broad divisions of information to progressively greater detail and specificity to discover vocational knowledge, interest and experience, configured such that indication of recognition of sensory stimuli in one deck guides selection of subsequent decks to obtain additional detail on vocational knowledge, interest and experience; and an automated analysis system that extracts and characterizes brain activation signals indicative of recognition of reproduced by the stimuli presentation/application system.

In this example, additional stimuli eliciting a response from other senses that may be reproduced and presented/applied to the test subject, including taste, smell and touch; the stimulus deck may be created by hand or by machine; the stimulus deck may be created before presentation/application or in real-time based on indications of recognition in previous stimulus decks; dealing the deck may be controlled by a stimulus dataset dealer or be automated; dealer control (in person or automation) may be proximal with the test subject or from a remote location; and/or the system may assess the level of test-subject cooperation and adjust recognition scores accordingly.

A recommendation engine will offer recommendations of areas of interest to the user perhaps not previously obvious to the user. The recommendation engine will identify concepts of interest through matching an interest signal present when participants are shown different concepts. An interest signal may be derived by measuring brain activity of a pre-selected group of participants in response to presentation of concepts. This pre-selected group also reports their level of interest in each concept either directly or indirectly, derived through some other way (such as 2-alternative forced-choice paradigm). The brain activity of the pre-selected group during high-interest concepts can be then used to derive an interest signal. New participants view concepts, and their brain activity is analyzed and matched for the interest signal. A stronger signal may indicate a greater level of interest.

The recommendation engine may employ several methods to classify responses into interest/no-interest. Concepts such as vacation destination can be represented by an n-dimensional vector. Concepts that are similar to each other are closer to each other in this n-dimensional space than concepts that are dissimilar to each other. Interest in a topic can be determined by measuring brain activity in response to the presentation of a concept. The recommendation engine can then sample level of interest in concept-space and move accordingly. High interest in a concept may indicate high interest in nearby (similar) concepts which may then be recommended. Rising interest upon moving from one concept to another may indicate a fruitful direction of motion through concept-space and concepts further in that direction may produce even greater interest. A decrease in interest upon moving from one concept to another may indicate declining interest. In this case, the recommendation engine can reverse course to search potentially more interesting concepts.

Figure 8A:
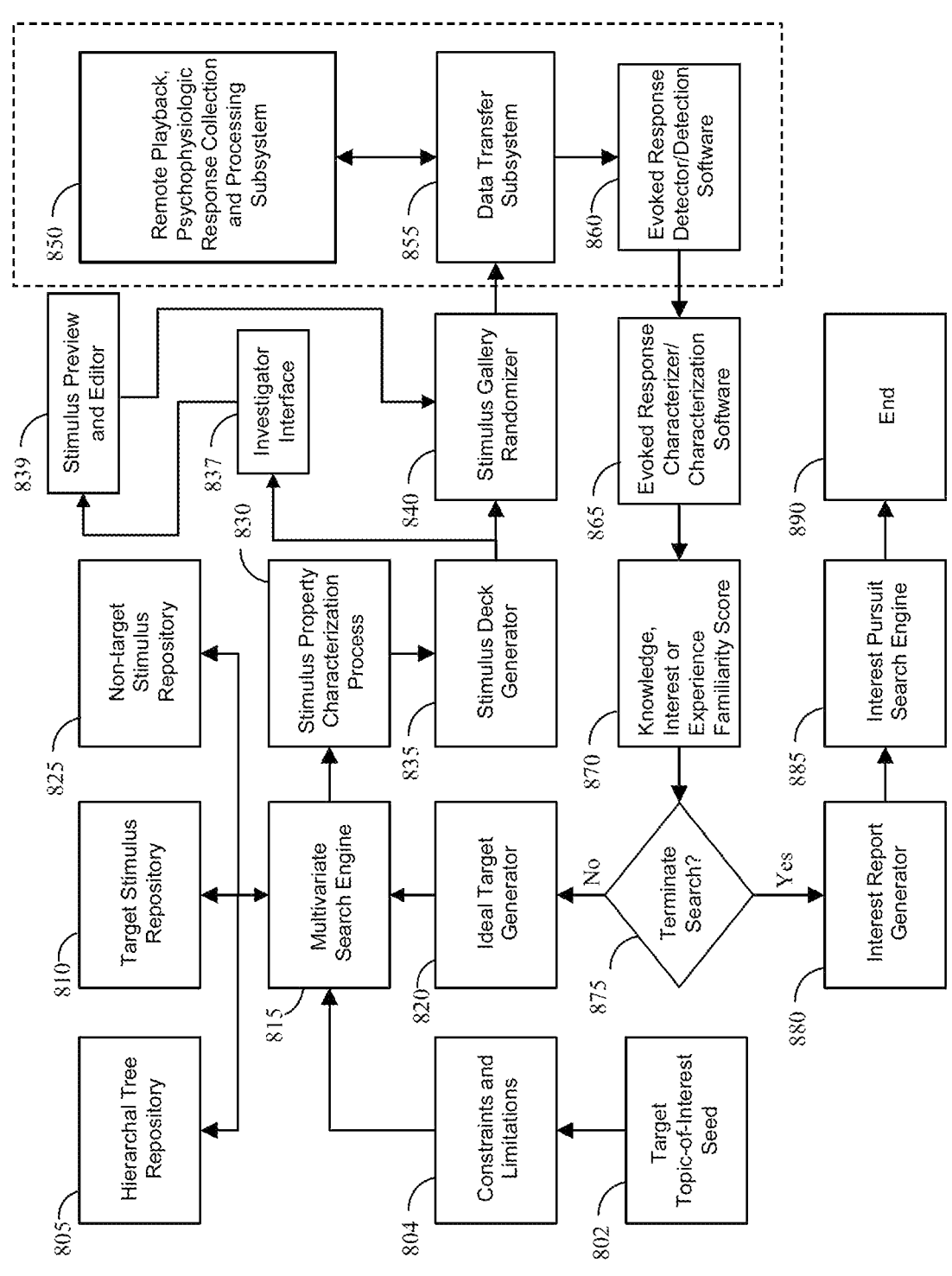
FIGS. 8A and 8B illustrate a logical flowchart diagram of a method of this disclosure in which topical interest of a subject is explored.
Figure 8B:
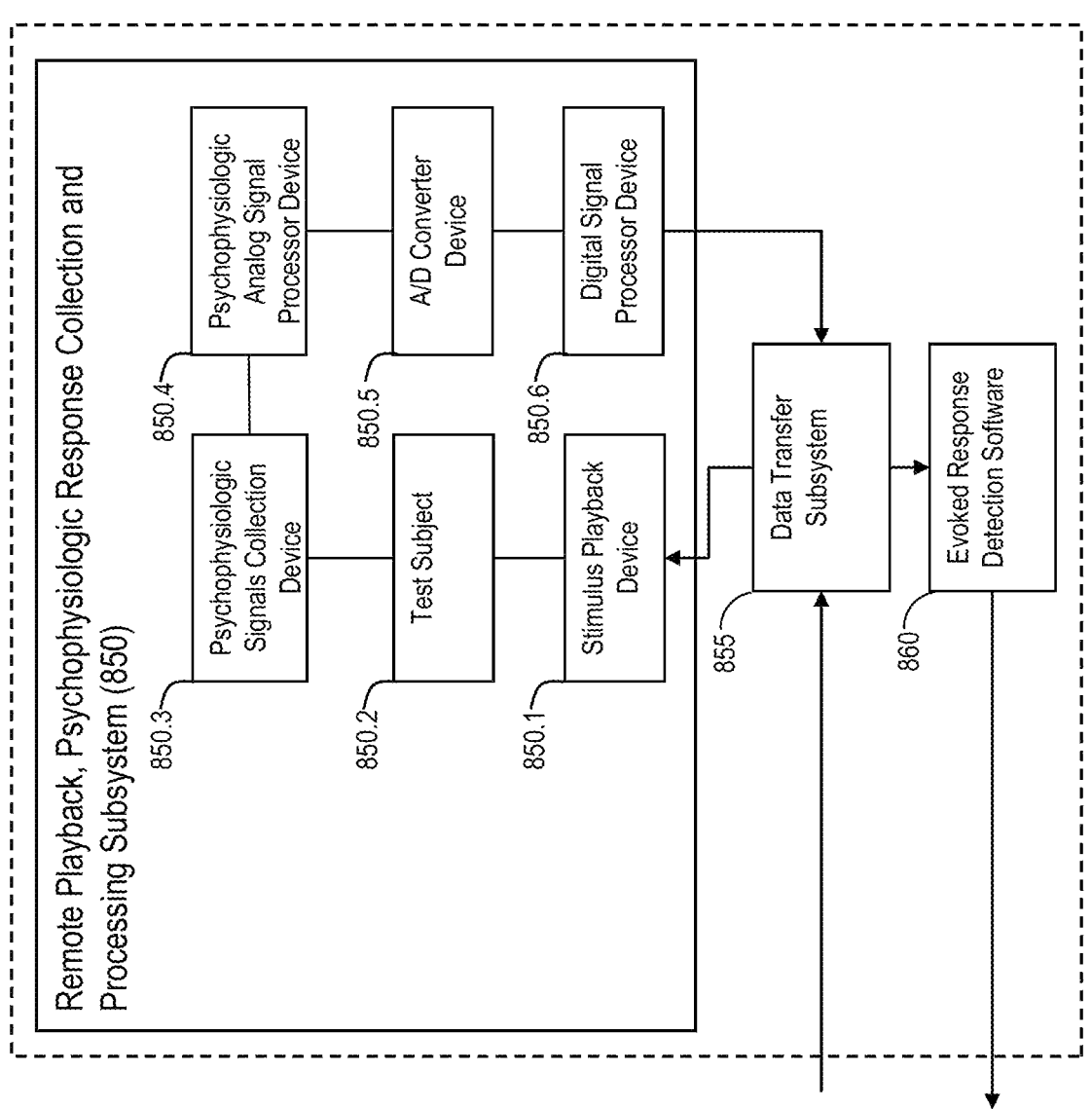

Alternatively, areas-of-interest of a person are explored by method 800 illustrated in the diagram of FIGS. 8A-8B. This method uses brain activation indications of interest to various facets of one or more areas-of-interest organized into a hierarchal tree structure with multiple levels of detail related to the area-of-interest. Similar to knowledge discovery, response to stimuli presented or applied to the user is associated with interest, directed attention and/or high positive valence revealed by EEG features such as the P300, N400, spatial analysis, spectral power analysis, signal entropy, and machine learning feature extraction techniques. By systematically evaluating the user's level of interest in the nodes of the hierarchal tree structure, the user is informed of specific areas-of-interest within the topic. In the hierarchal tree, the root node, or principal parent node, may have one or more child nodes each related to a subtopic of the root node. Children nodes may form a branch of the tree structure which is further populated by one or more child nodes which may form additional branches of progressively greater specificity of the parent subtopic. The tree structure may conform to any of the many tree structures used in computer science, set theory, taxonomy or family trees.

Figure 9:
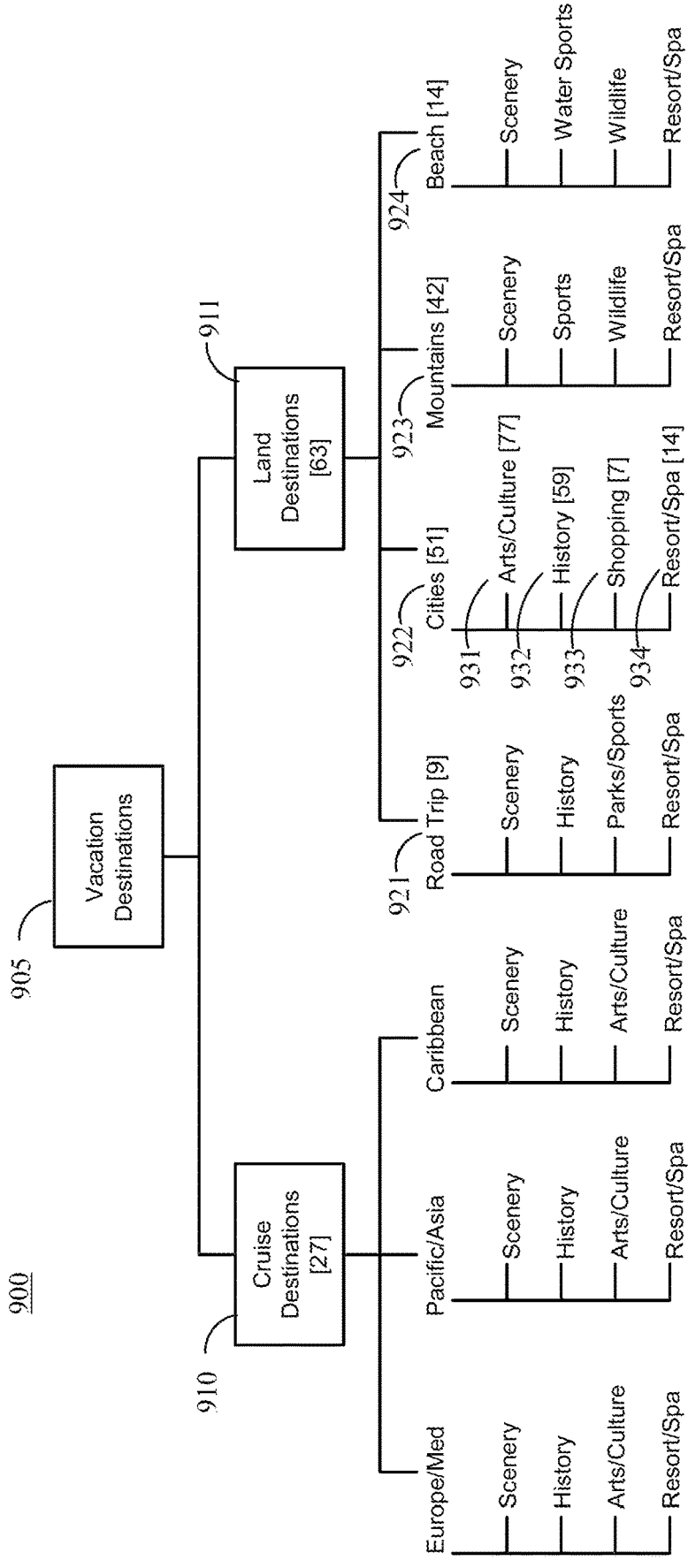
FIG. 9 illustrates one example of a hierarchal tree of a topic-of-interest several branches and sub-branches of sub-categories of a topic-of-interest.

For example, FIG. 9 illustrates a hierarchal topic tree 900 for a topic of vacation destinations 905. In practice, a plurality of hierarchal trees, (similar to hierarchal topic tree 900), are generated by the system operator prior to use in the system and are stored in a searchable, electronic database hierarchal tree repository 805 of FIGS. 8A-8B for later retrieval.

The root node of hierarchal tree 900 is the general topic-of-interest 905. The hierarchal tree 900 is composed of multiple branches and nodes on multiple levels. In this example, the tree root node 905 is vacation destinations. The tree root node 905 is subdivided into first-level children sub-categories cruise destinations 910 and land destinations 911 destinations in this example. First-level children nodes are parent nodes subdivided into one or more second-level children sub-categories such as the geographic locations, terrain types or other significant features of the destinations such as nodes 921 through 924; road trip, cities, mountains and beach respectively. Second-level parent nodes are further subdivided into third-level children categories of interest areas 931 to 934. In the example hierarchal tree 900, interest areas 932 and 934 are shared by other branches of the tree but that is not necessarily true for all hierarchal trees. In practice, the tree structure of an area-of-interest may be composed of a greater or smaller number of branches at each level and may have a larger or smaller number of levels as appropriate to the topic and desired degree of detail of the subcategories.

Method 800 of FIGS. 8A-8B is initiated by a user communicating a target topic-of-interest seed 802, to be explored. Target topic-of-interest seed 802 may be communicated by user input entered into a user-interface, provided by voice-to-text transcription at the user interface, selection of text or images displayed on the user interface or by other means. The user-interface may include a web browser or an input application executing on a general computing device or a mobile device. The target topic-of-interest seed 802 is passed to the constraints and limitations 804 query process. This process allows the user to express constraints or limitations of the topic-of-interest through answers to question and other forms of data entry through the user interface such as multiple-choice questions, free-form text entry, fill-in-the-blank, selection of icons and other mechanisms well-known in the art of computer interfaces. The purpose of the constraints and limitations process 804 is to place limitation(s) on the scope of searches performed by the multivariate search engine 815. The user may be prompted to identify the level of detail and scope of limitations and constraints of the subsequent search or the user may be prompted with specific questions related to the search. For the example of a topic for vacation destinations 905 of FIG. 9, the system may prompt the user to identify geographic exclusions, intended time of travel, excluded modes of transportation, preferred air carrier, preferred loyalty programs, cost limits, dietary preferences and the like.

In one example, the topic-of-interest and associated limitations and constraints are passed to the multivariate search engine 815 to identify previously prepared hierarchal trees-of-interest to inform the recommendation engine, (for example, 900, FIG. 9), stored in hierarchal tree repository 805. Other models describing the relationship between categories might also be employed by the recommendation engine. The one or more hierarchal trees most closely associated with the target topic-of-interest seed 802 returned by the multivariate search engine 815 identifies search criteria to populate a deck of sensory stimuli to explore the degree-of-interest of the user in each node of each level of the hierarchal tree.

Stimulus datasets are generated for each level of the hierarchal tree and presented to the user to assess the level of interest exhibited by the user for each of the stimuli. Method 800 may cycle through each of a plurality of hierarchal trees of interest returned by the multivariate search engine 815 in response to the target topic-of-interest seed 802 expressed by the user. For each hierarchal tree, one or more stimulus data sets may be created for each category in each level of the hierarchal tree.

By way of example, for a single hierarchical tree such as hierarchal tree 900 of FIG. 9, the tree topic 905 may be explored by sequentially exploring each of the first level subdivisions of the tree topic Vacation Destinations 905: Cruise Destinations 910 and Land Destinations 911. One or more stimulus data sets may be generated for first level of subdivision Cruise Destinations 910 and then another stimulus dataset for Land Destinations 911. The multivariate search engine 815 collects stimulus related to each of the nodes of the first level subdivision from the target stimulus repository 810. In this case, the search criteria may resemble "cruise vacations" and "land vacations." Stimuli returned by the multivariate search engine 815 may reflect the types of candidate stimuli populating the repository such as imagery, music, sounds and words. Stimuli returned for the "Cruise Destination" node of the first level subdivision may include images of cruise ships of various types and sizes (e.g., sail powered ships, small and large motorized cruise ships, riverboats, yachts, cruise ships), cruise ship amenities, seascapes, animals associated with the marine environment, famous landmarks or attractions associated with seaports frequented by cruise ships. Auditory stimuli included in the "Cruise Destination" node may include sounds of marine wildlife, surf on a beach, wind in the rigging of a sailboat, etc. Stimuli of the same types (e.g., imagery, sounds) but unrelated to the "Cruise Destinations" may also be collected from the non-target stimulus repository 825. The objective is to collect non-target stimuli that are close to the target category but not the same category as the target category. Features of brain activation indicative of interest may be more pronounced when stimuli eliciting interests are mixed with stimuli of appropriate non-interest or non-target stimuli. Target and non-target stimuli too far apart in similarity may result in a response of surprise in the user and thus create undesired noise in the EEG or other psychophysiological data. Examples of non-target stimuli for "Cruise Destinations" would be stimuli of non-water locations, for example, images of landscapes, famous landmarks associated with landlocked locations, ground transportation, land animals and sounds of land animals.

Target and non-target stimuli collected by the multivariate search engine 815 are communicated to the stimulus property characterization process 830 to assemble a subset of candidate stimuli that share consistency in presentation parameters such as color, resolution, brightness, contrast, saturation, cropping of images. Similarly, auditory stimuli would be evaluated for presentation parameters such as gain, duration, tempo, key, performing instruments. Stimulus modalities requiring more refined adjustments may require an operator interaction. Consistency of presentation parameters minimizes potential for spurious noise in the data created by psychophysiological responses caused by surprise or a data outlier event rather than the desired signal caused by test subject interest.

The stimulus deck generator 835 assembles a series of sensory stimuli for each iterative pass through the interest evaluation example in a dataset of target and non-target stimuli that satisfies the ratio of target and non-target components and assigns the dwell time for each stimulus for display based on the complexity of the stimuli and other parameters. When a stimulus dataset is presented to the test subject multiple times, the stimulus gallery randomizer 840 is used to randomize the dataset stimuli to ensure that the order of presentation does not introduce responses resulting from familiarity of the order of display. It is sometimes desirable to present the compiled dataset to the test subject more than once to provide multiple opportunities for the test subject to be exposed to the stimuli.

A stimulus dataset processed by the stimulus gallery randomizer 840 is communicated via a data transfer subsystem 855, (used to communicate information between subsystem components), to a remote presentation/application, psychophysiological response collection and processing subsystem 850, further illustrated in more detail in FIG. 8B. The data transfer subsystem 855 may include hardware and/or communication software that allows communication through, a local area network (LAN), a wide area network (WAN), an internet area network (IAN), and/or a computer network using Transmission Control Protocol (TCP) or Internet Protocol (IP) protocols to communicate between a plurality of networks and devices.

The remote subsystem 850 presents stimulus, received from the data transfer subsystem 855, to a stimulus presentation/application device 850.1 for presentation to a test subject 850.2, where EEG signals, i.e., psychophysiological response data of the subject collected from appropriate sensors, are received via an EEG signals collection device 850.3, where the signal data is converted via an A/D converter device 850.5, and further pre-processed, (e.g., down sampling, spectral filtering, artifact removal, referencing and epoching), at the EEG digital signal processing device 850.6.

In an alternative example, the devices and components of the remote system 850 may either in total or in part, be collocated with the devices and components enabling method 800 of FIG. 8A. Likewise, only a portion of the devices and components of remote system 850 may be remotely located from the devices and components of method 800 of FIG. 8A.

In a configuration where the signal of interest in the EEG data is an ERP, pre-processed data from the EEG digital signal processor device 850.6 are communicated to the evoked response detection software 860 which isolates brain activation evoked by the stimuli. Evoked response characterizer 865 extracts a knowledge, interest or experience familiarity score 870 for each stimulus presented in the stimulus gallery dataset.

After each stimulus dataset is presented and processed, the search termination decision point 875 is assessed. Example conditions leading to process termination are: having reached a set number of iterations (program parameter or user defined); datasets representing all nodes in all levels have been presented and evaluated by the system at least once; or, interest scores for multiple stimulus datasets representing high-scoring topics at each level have attained some minimum threshold of change indicating that the aggregate score has reached a plateau.

Another method using the recommendation engine may systematically follow the branch of a particular parent node with the highest interest score at each successive level. Exploring the tree structure may be approached by a combination of these two methods or other methods suitable for the character of the tree structure. Exploring the tree structure may be accomplished unidirectionally to successive levels of increased detail; always from parent to children nodes. It may also be accomplished in a bi-directional sense by allowing the search to move from child nodes back to parent nodes and move laterally within a level of siblings of the parent node and then down again to children nodes of the parent's siblings. The search may move more than one level up or down in the tree structure explore or re-explore branches of the tree structure.

The ideal target generator 820 may use interest scores 870 produced for each stimulus dataset presented to the user to associate the scores with the appropriate nodes of the one or more tree structures associated with the user's target topic-of-interest seed 802. As the interest scores 870 are reported and allocated to the nodes (for example, in FIG. 9, the interest scores allocated to particular nodes are denoted by bracketed numerals: [27] for node 910; [63] for node 911; [9] for node 921; [51] for node 922; [42] for node 923; [14] for node 924; [77] for node 931; [59] for node 932; [7] for node 933; and [14] for node 934), the ideal target generator 820 builds a model of the user's interest within the hierarchal tree structure and determines the search criteria to be used to further explore the hierarchal tree structure.

If, for example, the first two stimulus datasets in the process addressed subcategories "Cruises" and "Land" vacation destinations for nodes 910 and 911 of FIG. 9, respectively. By way of example, notional interest scores associated with nodes 910 and 911 are provided in parentheses below the names of the nodes. Using the notional interest scores, the ideal target generator would infer that land destinations were of more interest to the user and therefore instruct the multivariate search engine 815 to collect stimuli for children nodes 921 through 924 of the land 911 branch of tree 900. Interest scores resulting from presentation/application of datasets used to evaluate these nodes would cause the ideal target generator 820 to infer that node Cities 922 was of most interest among land destinations and therefore instruct the multivariate search engine 815 to collect stimuli for children nodes 931 through 934 of the cities branch of tree 900.

Other examples of using interest scores to model interest might include other representations of the relationships between categories, that account for overlapping features of interest between the categories and reveal new categories of features of similarity between categories. For example, stimuli might be grouped together in different ways. A person might be equally interested in "Cruises" and "Land" vacations because both might include a "Culinary" experience as revealed by high interest scores of stimuli including food.

Interest scores 870 returned for these nodes cause the ideal target generator 820 to infer that the user is most interested in arts and culture, i.e., node 931 having an allocated interest score of [77], associated with cities, (node 922), with a close secondary interest in history of cities, i.e., node 932 having an allocated interest score of [59]. In practice, the tree structure 900 may be extended with branches to children nodes below parent nodes of city activities arts/culture 931 and history 932. Such nodes might include geographic regions and/or cities which may be further explored for specific art, culture or history attractions such as museums, art galleries or historic sites. For each node explored, the multivariate search engine 815 may pull appropriate stimuli from the target and non-target stimulus repositories 810 and 825 for generation, display and interest evaluation by the system until the interest exploration session is terminated.

Upon termination of the interest exploration session, the results of the interest survey are prepared by the interest report generator 880. The level of detail contained in the report may range from a simple conclusion of the interest survey to a detailed report that might include presentation of the hierarchal tree or other graphical representations of results generated by the recommendation engine using other algorithms, the nodes explored, interest scores associated with the nodes, and the path through the tree leading to the conclusions of the survey. Using the example above, a simple report may be as simple as a statement, "Your preferred vacation destination is a tour of art galleries in Washington, DC." The report may be presented as text, graphics, a video or short commercia or a combination thereof. The report may be delivered as computer readable files, electronic display or hard-copy printouts.

Conclusions drawn from the interest survey may be used to guide pursuit of the revealed interests. The user may further investigate the revealed interest areas manually or use a computer assisted interest pursuit search engine 885. Using the example of an interest survey based on the topic of vacation destinations, the contents of the interest report generator 880 may be used to guide the search for commercial vacation packages bundling transportation, lodging and admission tickets to venues targeted for the high-scoring vacation interests. Similarly, the user may create a personalized vacation package by selecting from options for transportation, lodging and venues identified by user-directed manual or automated search. Packages or components of a vacation package may be purchased or reserved for later purchase using any means well known in the art. Regardless of the search topic, results of the interest survey enable the user to further investigate revealed details of the general area-of-interest.

Figure 10:
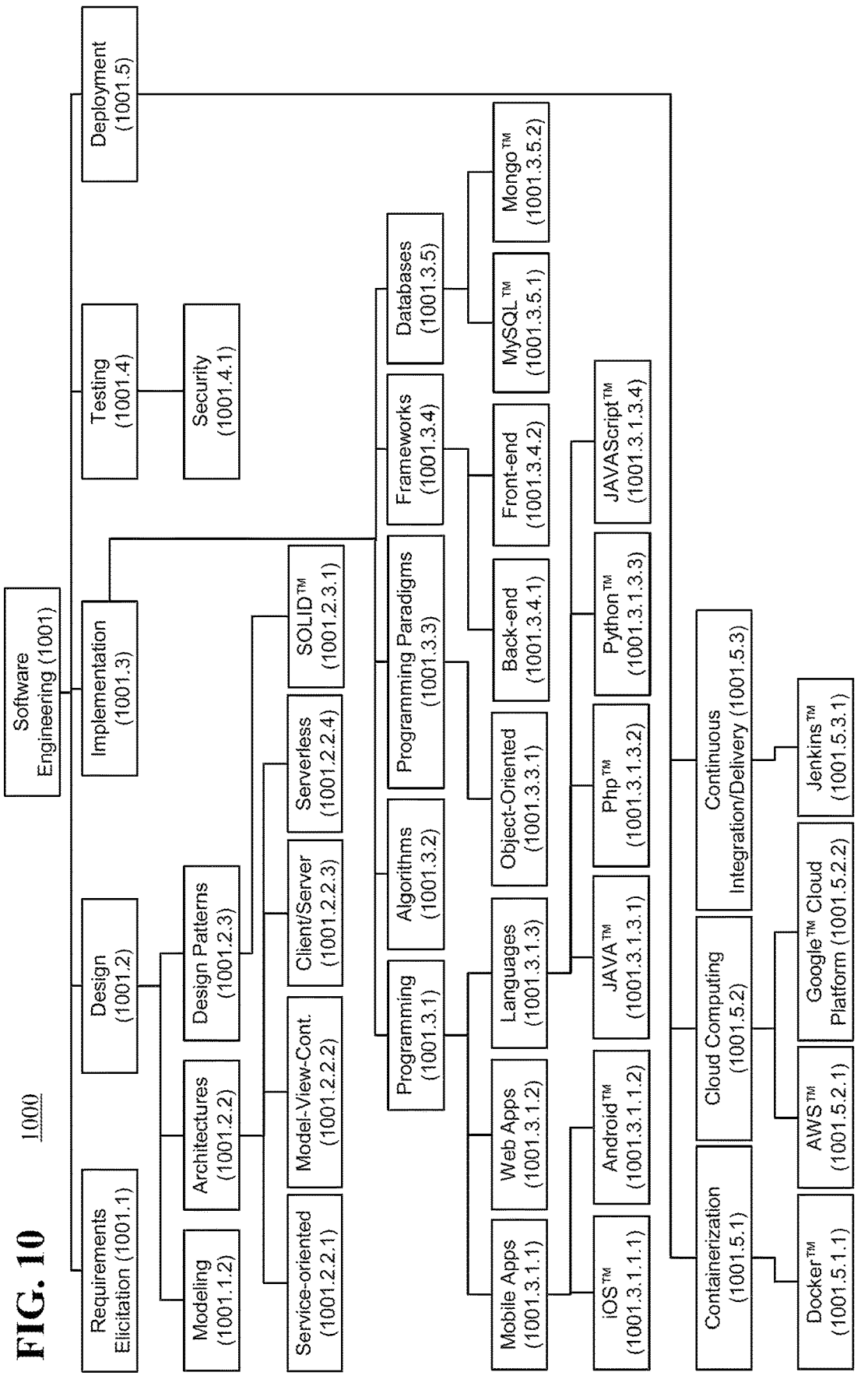
FIG. 10 illustrates another example of a hierarchal tree of a topic-of-interest several branches and sub-branches of sub-categories of another topic-of-interest.

FIG. 10 depicts another example wherein stimulus decks may be generated to validate and/or probe deeper levels of a subject's knowledge, interest or experience of subject matter related to a predetermined hierarchal topic tree structure 1000. In this example, a topic tree topic node, e.g., "Software Engineering" 1001, is chosen from the hierarchal tree repository 805, (see FIG. 8A), and stimuli may by chosen from target stimuli repository 810 and non-target stimuli 825 based on the hierarchal topic tree structure 1000 to validate and/or probe a subject's knowledge, interest or experience in the broad field of software engineering. Stimuli for each node of the hierarchal topic tree structure 1000 may be predetermined, or in the alternative, may be chosen with assistance of the multivariate search engine 815 that may use a topical identifier of a node in the hierarchal topic tree structure 1000 to generate stimuli for the respective node, or to assist in choosing stimuli from the target 810 and non-target 825 stimulus repositories.

Stimuli may be characterized by characterization process 830 and made accessible to the stimulus deck generator 835 that draws a sequence of sensory stimuli and sends the sequence to the randomizer 840. Optionally, a user may access the sequence of sensory stimuli through the investigator interface 837 and edit the sequence through the stimulus preview and editor 839.

The stimuli, via the data transfer subsystem 855, (see FIGS. 8A-8B), are then presented via the stimulus presentation/application device 850.1 to the test subject 850.2 (see FIG. 8B), and the test subject's EEG signals are collected by the EEG signals collection device 850.3, analog processed by the EEG analog signal processor device 850.4, converted by the A/D converter device 850.5, and digitally processed by the EEG digital signal processor device 850.6. The P-300 signal(s) as an example of a feature of interest of the EEG data may be communicated back to the data transfer subsystem 855 and detected by the evoked response detector/detection software 860, characterizer/characterization software 865, and given a knowledge, interest or experience familiarity score 870 for each node of the hierarchal topic tree structure 1000 presented to the subject.

FIG. 10 illustrates an example where processing is not terminated until a knowledge, interest or experience familiarity score 870 is associated with each node of every branch and level of the hierarchal topic tree structure 1000. A hierarchal topic tree structure 1000 of any type can be systematically explored to test a subject on every node of all branches and all levels, whereby the system may determine a depth of knowledge of a subject associated with a particular topic tree topic node 1001 by determining a knowledge, interest or experience familiarity scores in all nodes of the hierarchal topic tree structure 1000.

FIG. 10 illustrates an example of a hierarchal topic tree structure 1000 having a topic tree topic node 1001 of "Software Engineering." A first level contains five branch topic nodes: Requirements Elicitation 1001.1; Design 1001.2; Implementation 1001.3; Testing 1001.4; and, Deployment 1001.5. Each of the first level branch topic nodes may have no further topic nodes at a lower level, for example, Requirements Elicitation 1001.1, or may have a plurality of topic sub-nodes, (or child nodes), arranged in sub-levels and branches, for example, Implementation 1001.3, having child nodes at a next level, Programming 1001.3.1 to Languages 1001.3.1.3 to JAVA™ 1001.3.1.3.1.

The above method may test a candidate subject on their knowledge, interest or experience on each or any determined node or nodes of a tree structure, for example, hierarchal topic tree structure 1000, and based on a subject's elicited psychophysiological response to stimuli corresponding to a particular tree structure node, the system may generate a corresponding knowledge, interest or experience familiarity score for that particular node.

The system may further present node-specific stimuli corresponding to a portion of nodes of the hierarchal topic tree structure 1000 or to all the nodes of the hierarchal topic tree structure 1000. Based on the elicited psychophysiological response to the presented stimuli and corresponding knowledge, interest or experience familiarity scores for those particular nodes, the system may further perform a method of determining the depth of knowledge of a subject corresponding to the hierarchal topic tree structure 1000 by presenting a combined average score of either all or a substantial portion of the familiarity scores of the particular topic tree structure. For example, with respect to FIG. 10, the system may take all the knowledge, interest or experience familiarity scores for each node under the topic tree topic node "Software Engineering" 1001 of hierarchal topic tree structure 1000, i.e., from the first level Requirements Elicitation 1001.1 node to the last level and last branch Jenkins™ 1001.5.3.1 node.

The system may further determine average familiarity scores for one or a group of particular vertical branches of nodes within the topic tree structure, for example, a branch familiarity score for the JavaScript™ node 1001.3.1.3.4 that includes the averages of the Implementation node 1001.3, the Programming node 1001.3.1, the Languages node 1001.3.1.3, and the JavaScript™ node 1001.3.1.3.4.

The system may further determine average familiarity scores for particular levels of nodes within the topic tree structure, for example, a level familiarity score for the third level of nodes under the Architectures node 1001.2.2, i.e., the Service-oriented node 1001.2.2.1, the Model-View-Cont. node 1001.2.2.2, the Client/Server node 1001.2.2.3, and the Serverless node 1001.2.2.4. The average familiarity scores for the common level of nodes may be stored in the system independently of the above parent node, or the parent node may store the value of the average familiarity scores of its child nodes.

In another example, the instant application teaches a method capable of deducing the vocation of an individual without prior knowledge and without engaging a person in verbal questions. The method is enabled by a system composed of an EEG subsystem, a stimulus presentation/application subsystem, a system of stored records of stimuli and an automated data processing subsystem. The EEG subsystem is composed of multiple channels of sensors, amplifiers, analog filters and analog-to-digital converters. The stimulus presentation/application subsystem may reproduce multiple records of images, video, or sounds stored in analog or digital files that form decks of stimulus data. The stimulus presentation/application system is synchronized with the EEG system so that the time of presentation and identity of the stimulus record are associated with the EEG or other psychophysiological data. The subject is exposed rapidly to sensory stimuli, and the elicited psychophysiological response is recorded by the EEG subsystem. The automated data processing system extracts and characterizes brain activation from EEG or other psychophysiological data to indicate the level of recognition of each stimulus. Multiple stimulus decks are presented in a systematic approach starting with broad divisions of information to progressively greater detail and specificity to discover vocational knowledge, interest, and experience of the person being monitored. Indication of recognition of sensory stimuli in one deck guides automated selection of subsequent decks to obtain additional detail on vocational knowledge, interest, and experience.

All or part of the methods described herein may be implemented as a computer program product that is a non-transitory computer-readable storage medium encoded with computer code that is executable by a processor. All or part of the systems and methods described in this application may be implemented as an apparatus, method, or electronic system that may include one or more processors and storage devices that store executable computer program code to implement the stated functions.

The details of one or more examples of the subject matter of this application are set forth in the drawings and descriptions contained in this application. Other features, aspects, and advantages of the subject matter may become apparent from the description above, drawings, and claims.

The subject matter of this specification functions in a variety of component combinations and contemplates all those types of components a person of ordinary skill in the art would find suitable for functions performed. The figures describe specific components in specific examples. However, the range of the types of components mentioned in the description of the figures may be applied to other examples as well.

The terminology used herein is for the purpose of describing particular examples only and is not intended to be limiting. As used herein, the singular forms "a," "an," and "the" are intended to include the plural forms as well, unless the context clearly indicates otherwise. The terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The subject matter of this specification is described above with reference to system diagrams, flow diagrams, and screen mockups of systems, methods, and computer program products. Each block or combinations of blocks in the diagrams may be implemented by computer program code and may represent a module, segment, or portion of code. Program code may be written in any combination of one or more programming languages, including object-oriented programming languages such as the JAVA®, SMALL-TALK®, C++, C#, OBJECTIVEC® programming languages and conventional procedural programming languages, such as the "C" programming language.

It should be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It may also be noted that each block or combination of blocks in the diagrams may be implemented by special purpose hardware-based systems that perform the specified functions or acts.

Computer program code may be provided to a processor or multiple processors of a computer to produce a particular machine, such that the program code, which executes via the processor, create means for implementing the functions specified in the system diagrams, flow diagrams, and screen mockups.

The subject matter of this specification may be implemented on one or more physical machines. Each physical machine may be a computer comprising one or more processors and one or more storage devices; however, a single processor and a single storage device are sufficient. A person of ordinary skill in the art may recognize the variety of types of computers suitable for the functions described, including desktops, laptops, handset devices, smartphones, tablets, servers, or accessories incorporating computers such as watches, glasses, or wearable computerized shoes or textiles. A non-exhaustive list of specific examples of computers includes the following: Dell ALIENWARE™ desktops, Lenovo THINKPAD® laptops, SAMSUNG™ handsets, Google ANDROID™ smartphones, Apple IPAD® tablets, IBM BLADECENTER® blade servers, PEBBLE™ wearable computer watches, Google GLASS™ wearable computer glasses, or any other device having one or more processors and one or more storage devices, and capable of functioning as described in this application.

A processor may be any device that accepts data as input, processes it according to instructions stored in a storage component, and provides results as output. A person of ordinary skill in the art may recognized the variety of types of processors suitable for the functions disclosed, including general purpose processing units and special purpose processing units. A non-exhaustive list of specific examples of processors includes the following: Qualcomm SNAP-DRAGON™ processors; Nvidia TEGRA® 4 processors; Intel CORE™ i3, i5, i7 and i9 processors; TEXAS INSTRUMENTS™ OMAP4430; ARM® Cortex-M3; and AMD OPTERON™ 6300, 4300, and 3300 Series processors. Each computer may have a single processor or multiple processors operatively connected either physically or via a network, (e.g. in the "cloud").

A storage device is any type of non-transitory computer readable storage medium. A person of ordinary skill in the art may recognized the variety of types of storage devices suitable for the functions disclosed, including any electronic, magnetic, optical, electromagnetic, infrared, or semiconductor system or device, so long as it does not reduce to a transitory or propagating signal. A non-exhaustive list of specific examples of storage devices includes the following: portable computer diskettes, hard disks, random access memory, read-only memory, erasable programmable read-only memory, flash memory, optical fibers, portable compact disc read-only memory, optical storage devices, and magnetic storage devices. Each computer may have a single storage device or multiple storage devices operatively connected (e.g. in the "cloud").

This disclosure may be implemented on one or more computers running one or more instances of a virtual machine. A virtual machine is a software implementation of a computer that executes programs like a physical machine. Thus, a single physical machine may function conventionally as a physical computer, while also implementing a virtual machine that may perform the same processes as the physical computer. Multiple instances of a virtual machine may run on one computer or across multiple computers. A person of ordinary skill in the art may recognize the variety of types of virtual machines suitable for the functions disclosed, including system level virtual machines, process level virtual machines, fictive computers, and distributed computers. A non-exhaustive list of specific examples of virtual machines includes the following: VMWARE® virtual machines and Oracle VM VIRTUALBOX™ virtual machines.

Examples of this disclosure that employ virtual machines may contain a hypervisor, which is also known as a virtual machine monitor. A hypervisor is a piece of computer software that creates, runs, and manages virtual machines. More than one virtual machine may be run by a single hypervisor. The hypervisor controls the utilization of one or more processors by one or more virtual machines and the utilization of one or more storage devices by one or more virtual machines. A person of ordinary skill in the art may recognized the variety of types of hypervisors suitable for the functions disclosed, including type one or "native" hypervisors, and type two or "hosted" hypervisors. A non-exhaustive list of specific examples of hypervisors includes: Oracle VMWARE® Server for SPARC, Oracle VM SERVER™ for x86, Citrix XENSERVER™, and VMWARE® ESX/ESXi.

For the purposes of this application, the term "computing component" means a computer, a virtual machine, or multiple computers or virtual machines functioning as a single component. The term "computer" is limited to physical machines. Generally, a computer functions as a computing component by implementing an operating system through which program code, which implements the methods of this system, is executed. Generally, when a virtual machine functions as a computing component, a computer implements a hypervisor which implements a separate operating system, through which the program code is executed.

As referenced above, a single computer may implement multiple computing components, wherein the computer itself functions as a computing component and concurrently implements one or more instances of a virtual machine. Each virtual machine functions as a separate computing component. Similarly, a plurality of computing components may be made up of separate computers, none of which implement a virtual machine, or a plurality of computing components may be implemented on a single computer wherein only the virtual machines function as computing components. Additional combinations are contemplated as well, such as where a computing component is implemented across multiple computers. For example, a hypervisor of a virtual machine may manage the processors and storage devices of three computers to implement a virtual machine that functions as a single computing component. A person of ordinary skill in the art may recognize the range of combinations of computers and virtual machines that are suitable for the functions disclosed.

Computing components may be operatively connected to one another or other devices, such as by a communications network. One skilled in the art may recognize the appropriate media over which multiple computing components may be operatively connected to each other in a manner suitable for the functions disclosed, including as a communications network that allows the computing components to exchange data such that a process in one computing component is able to exchange information with a process in another computing component. A non-exhaustive list of specific examples of transmission media includes serial or parallel bus systems, wireless, wireline, twisted pair, coaxial cable, optical fiber cable, radio frequency, microwave transmission, or any other electromagnetic transmission media.

The above components are described in greater detail with reference to the figures. The descriptions set forth the various processes, relationships, and physical components of various examples of the subject matter of this disclosure.

The invention claimed is:

1. A method for obtaining information of at least one of knowledge, interest and experience of a subject for a specific category related to one of a topic of knowledge, familiarity or interest, the method comprising:

generating a first stimulus at a first location and communicating the first stimulus through a data transfer subsystem to a stimulus playback device at a second remote location;

receiving, by a first processor, a first psychophysiological signal, wherein the first psychophysiological signal represents a first psychophysiological response of the subject to the first stimulus presented at the stimulus playback device;

communicating the first psychophysiological response through the data transfer subsystem and detecting, at a second processor, a first evoked response potential (ERP) characterization of the first psychophysiological response;

determining, by the second processor, a first correlation between the first ERP characterization and a category related to one of a topic of knowledge, familiarity or interest;

based on determining the first correlation between the first ERP characterization and the category related to one of the topic of knowledge, familiarity or interest, selecting, at the first location, a second stimulus related to a sub-category of the category related to one of the topic of knowledge, familiarity or interest;

communicating the second stimulus through the data transfer subsystem to the stimulus playback device at the second remote location;

receiving, by the first processor, a second psychophysiological signal, wherein the second psychophysiological signal represents a second psychophysiological response of the subject to the second stimulus presented at the stimulus playback device;

communicating the second psychophysiological response through the data transfer subsystem and detecting, at the second processor, a second evoked response potential (ERP) characterization of the second psychophysiological response;

determining, by the second processor, a second correlation between the second ERP characterization and the sub-category of the category related to one of the topic of knowledge, familiarity or interest; and obtaining information of at least one of knowledge, interest and experience of the subject based on the determined second correlation between the second ERP characterization and the sub-category of the category related to one of the topic of knowledge, familiarity or interest.

2. The method of claim 1, wherein said first and second stimulus are comprised of at least one of an external stimuli, an internal stimuli, and task stimuli.

3. The method of claim 1, wherein said first and second psychophysiological signals includes at least one of a neurophysiological response, a psychophysiological response, a psychological response, a psychophysical response, and a physiological change.

4. The method of claim 1, wherein a location of determining the first correlation and selecting the second stimulus is located remotely from the remote location where the first and second psychophysiological signals are collected from the subject.

* * * * *